US00RE49056E

(19) United States
(12) Reissued Patent
Tal et al.

(10) Patent Number: US RE49,056 E
(45) Date of Reissued Patent: May 3, 2022

(54) ACCESS DEVICE

(71) Applicant: Smiths Medical ASD, Inc., Plymouth, MN (US)

(72) Inventors: Michael Tal, Woodbridge, CT (US); Janelle Anderson, New York, NY (US); Benjamin K. Yaffe, San Francisco, CA (US); William J. McCreight, Harleysville, PA (US); Robert Rabiner, Tiverton, RI (US)

(73) Assignee: SMITHS MEDICAL ASD, INC., Plymouth, MN (US)

(21) Appl. No.: 16/743,406

(22) Filed: Jan. 15, 2020

Related U.S. Patent Documents

Reissue of:
(64) Patent No.: 8,377,006
Issued: Feb. 19, 2013
Appl. No.: 13/084,440
Filed: Apr. 11, 2011

U.S. Applications:
(63) Continuation of application No. 12/019,598, filed on Jan. 24, 2008, now Pat. No. 7,922,696.
(Continued)

(51) Int. Cl.
*A61M 5/178* (2006.01)
*A61M 25/06* (2006.01)
(Continued)

(52) U.S. Cl.
CPC ..... *A61M 25/0606* (2013.01); *A61B 17/34* (2013.01); *A61B 17/3496* (2013.01); *A61M 25/0097* (2013.01); *A61B 2017/347* (2013.01)

(58) Field of Classification Search
CPC ..... A61M 25/0097; A61M 25/0612; A61M 25/0631; A61M 25/01; A61M 25/0102; A61B 2017/347
See application file for complete search history.

(56) References Cited

U.S. PATENT DOCUMENTS 500,740 A 7/1893 Doyle
1,436,882 A 11/1922 Knepper
(Continued)

FOREIGN PATENT DOCUMENTS

DE 2052364 A1 4/1972
DE 8915299 U1 2/1990
(Continued)

OTHER PUBLICATIONS

U.S. Appl. No. 12/106,196, filed Apr. 18, 2008, now U.S. Pat. No. 8,105,286, issued on Jan. 31, 2012, by Janelle Anderson, et al., Notice of Allowance dated Sep. 28, 2011.
(Continued)

*Primary Examiner* — Catherine S Williams
(74) *Attorney, Agent, or Firm* — Benesch, Friedlander, Coplan & Aronoff LLP

(57) ABSTRACT

An access device places a medical article within a body space of a patient. The device has a needle section that includes an elongated body and a needle hub. The device further includes a dilator portion that has a dilator and a dilator hub. The dilator is coaxially disposed and slideable over the elongated body of the needle section. The device further includes a sheath section that has a sheath and a sheath hub. The sheath is coaxially disposed and slideable over the dilator. The device further includes a first locking mechanism operably disposed between the needle hub and the dilator hub to inhibit at least unintentional axial movement between the needle section and the dilator portion and a second locking mechanism operably disposed between the dilator hub and the sheath hub to inhibit at least unintentional axial movement between the dilator portion and the sheath section.

4 Claims, 23 Drawing Sheets

Related U.S. Application Data

(60) Provisional application No. 60/886,443, filed on Jan. 24, 2007.

(51) Int. Cl.
*A61B 17/34* (2006.01)
*A61M 25/00* (2006.01)

(56) References Cited

U.S. PATENT DOCUMENTS 3,185,152 A 5/1965 Ring
3,539,034 A 11/1970 Tafeen
3,540,447 A 11/1970 Howe et al.
3,565,074 A 2/1971 Foti et al.
3,670,729 A 6/1972 Bennett et al.
3,680,562 A 8/1972 Wittes
3,993,079 A 11/1976 Gatztanondo
3,995,628 A 12/1976 Gula et al.
4,068,659 A 1/1978 Moorehead
4,068,660 A 1/1978 Beck
4,072,146 A 2/1978 Howes
4,170,993 A 10/1979 Alvarez
4,191,186 A 3/1980 Keeler
4,192,305 A 3/1980 Seberg
4,205,675 A 6/1980 Vaillancourt
4,230,109 A 10/1980 Geiss
4,230,123 A 10/1980 Hawkins, Jr.
4,230,675 A 10/1980 Yarbro
4,231,367 A 11/1980 Rash
4,233,974 A 11/1980 Desecki et al.
4,241,019 A 12/1980 Nakatani et al.
4,274,408 A 6/1981 Nimrod
4,289,450 A 9/1981 Kling
4,311,137 A 1/1982 Gerard
4,333,505 A 6/1982 Jones et al.
4,345,596 A 8/1982 Young
4,411,655 A 10/1983 Schreck
4,412,832 A 11/1983 Kling et al.
4,417,886 A 11/1983 Frankhouser et al.
4,445,893 A 5/1984 Bodicky
4,512,351 A 4/1985 Pohndorf
4,525,157 A 6/1985 Vaillancourt
4,539,003 A 9/1985 Tucker
4,581,019 A 4/1986 Curelaru et al.
4,610,665 A 9/1986 Matsumoto et al.
4,629,450 A 12/1986 Suzuki et al.
4,652,256 A 3/1987 Vaillancourt
4,655,750 A 4/1987 Vaillancourt
4,661,300 A 4/1987 Daugherty
4,752,292 A 6/1988 Lopez et al.
4,756,230 A 7/1988 Shew
4,772,264 A 9/1988 Cragg
4,791,937 A * 12/1988 Wang ..... 600/565
4,826,486 A 5/1989 Palsrok et al.
4,850,960 A 7/1989 Grayzel
4,850,975 A 7/1989 Furukawa
4,869,259 A 9/1989 Elkins
4,894,052 A 1/1990 Crawford
4,917,669 A 4/1990 Bonaldo
4,917,679 A 4/1990 Kronner
4,944,728 A 7/1990 Carrell
4,950,252 A 8/1990 Luther et al.
4,952,207 A 8/1990 Lemieux
4,955,890 A 9/1990 Yamamoto et al.
4,961,729 A 10/1990 Vaillancourt
4,978,334 A 12/1990 Toye et al.
4,995,866 A 2/1991 Amplatz et al.
4,997,421 A 3/1991 Palsrok et al.
5,045,065 A 9/1991 Raulerson
5,049,136 A 9/1991 Johnson
5,053,017 A 10/1991 Chamuel
5,059,186 A 10/1991 Yamamoto et al.
5,064,414 A 11/1991 Revane
5,066,284 A 11/1991 Mersch et al.
5,067,945 A 11/1991 Ryan et al.
5,098,389 A 3/1992 Cappucci
5,098,392 A * 3/1992 Fleischhacker et al. ..... 604/164.05
5,102,394 A 4/1992 Lasaitis et al.
5,105,807 A 4/1992 Kahn et al.
5,108,374 A 4/1992 Lemieux
5,112,308 A 5/1992 Olsen et al.
5,114,401 A 5/1992 Stuart et al.
5,124,544 A 6/1992 Ohzu
5,135,502 A 8/1992 Koenig, Jr. et al.
5,135,505 A 8/1992 Kaufman
5,158,544 A 10/1992 Weinstein
5,167,637 A 12/1992 Okada et al.
5,171,218 A 12/1992 Fonger et al.
5,212,052 A 5/1993 Sakanoue et al.
5,215,525 A 6/1993 Sturman
5,215,528 A 6/1993 Purdy et al.
5,242,410 A 9/1993 Melker
5,242,414 A 9/1993 Fischell et al.
5,242,427 A * 9/1993 Bilweis ..... 604/264
5,246,426 A 9/1993 Lewis et al.
5,248,301 A 9/1993 Koenig, Jr. et al.
5,248,306 A 9/1993 Clark et al.
5,250,038 A 10/1993 Melker et al.
5,255,691 A 10/1993 Otten
5,279,590 A 1/1994 Sinko
5,295,969 A 3/1994 Fischell
5,295,970 A 3/1994 Clinton et al.
5,306,253 A 4/1994 Brimhall
5,312,355 A 5/1994 Lee
5,312,359 A 5/1994 Wallace
5,314,411 A 5/1994 Bierman et al.
5,328,480 A 7/1994 Melker et al.
5,330,433 A 7/1994 Fonger et al.
5,334,149 A 8/1994 Nortman et al.
5,334,157 A 8/1994 Klein et al.
5,336,191 A 8/1994 Davis et al.
5,342,315 A 8/1994 Rowe et al.
5,366,441 A 11/1994 Crawford
5,380,290 A 1/1995 Makower et al.
5,388,589 A 2/1995 Davis
5,391,152 A 2/1995 Patterson
5,391,178 A 2/1995 Yapor
5,397,311 A 3/1995 Walker et al.
5,403,283 A 4/1995 Luther
5,419,766 A 5/1995 Chang et al.
5,424,410 A 6/1995 Payne et al.
5,425,718 A 6/1995 Tay et al.
5,468,024 A 11/1995 Carman et al.
5,512,052 A 4/1996 Jesch
5,520,654 A 5/1996 Wahlberg
5,531,701 A 7/1996 Luther
5,531,713 A 7/1996 Mastronardi et al.
5,542,932 A 8/1996 Daugherty
5,558,132 A 9/1996 Haeussler et al.
5,562,634 A 10/1996 Flumene
5,589,120 A 12/1996 Khan et al.
5,676,653 A 10/1997 Taylor et al.
5,676,658 A 10/1997 Erskine
5,676,689 A 10/1997 Kensery et al.
5,685,856 A 11/1997 Lehrer
5,688,249 A 11/1997 Chang et al.
5,688,570 A 11/1997 Ruttinger
5,690,619 A 11/1997 Erskine
5,704,914 A 1/1998 Stocking et al.
5,712,229 A 1/1998 Hopkins et al.
5,713,876 A 2/1998 Bogert et al.
5,728,132 A 3/1998 Van Tassel et al.
5,749,857 A 5/1998 Cuppy
5,795,339 A 8/1998 Erskine
5,810,780 A 9/1998 Brimhall et al.
5,820,596 A 10/1998 Rosen et al.
5,827,202 A 10/1998 Miraki et al.
5,830,190 A 11/1998 Howell
5,833,662 A 11/1998 Stevens
5,853,393 A 12/1998 Bogert
5,858,002 A 1/1999 Jesch
5,865,806 A 2/1999 Howell
5,885,217 A 3/1999 Gisselberg et al.

(56) References Cited

U.S. PATENT DOCUMENTS 5,885,253 A 3/1999 Liu
5,885,283 A 3/1999 Liu
5,902,254 A 5/1999 Magram
5,904,657 A 5/1999 Unsworth et al.
5,910,132 A 6/1999 Schultz
5,911,705 A 6/1999 Howell
5,919,160 A 7/1999 Sanfilippo
5,935,110 A 8/1999 Brimhall
5,954,698 A 9/1999 Pike
5,954,708 A 9/1999 Lopez et al.
5,957,894 A 9/1999 Kerwin et al.
5,984,895 A 11/1999 Padilla et al.
6,004,294 A 12/1999 Brimhall et al.
6,027,480 A 2/2000 Davis et al.
6,046,143 A 4/2000 Khan et al.
6,074,377 A 6/2000 Sanfilippo
6,080,137 A 6/2000 Pike
6,080,141 A 6/2000 Castro et al.
6,117,108 A 9/2000 Woehr et al.
6,117,140 A 9/2000 Munsinger
6,120,460 A 9/2000 Abreu
6,120,494 A 9/2000 Jonkman
6,137,468 A 10/2000 Martinez et al.
6,156,010 A 12/2000 Kuracina et al.
6,159,179 A 12/2000 Simonson
6,179,813 B1 1/2001 Ballow et al.
6,179,823 B1 1/2001 Niedospial, Jr.
6,210,332 B1 4/2001 Chiao et al.
6,210,366 B1 4/2001 Sanfilippo
6,245,044 B1 6/2001 Daw et al.
6,273,871 B1 8/2001 Davis et al.
6,277,100 B1 8/2001 Raulerson
6,287,278 B1 9/2001 Woehr et al.
6,287,322 B1 9/2001 Zhu et al.
6,328,717 B1 12/2001 Solomon et al.
6,336,914 B1 * 1/2002 Gillespie, III ..... 604/165.01
6,379,333 B1 4/2002 Brimhall et al.
6,436,070 B1 8/2002 Botich et al.
6,461,362 B1 10/2002 Halseth et al.
6,475,207 B1 11/2002 Maginot
6,488,662 B2 12/2002 Sirimanne
6,500,152 B1 12/2002 Illi
6,524,277 B1 * 2/2003 Chang ..... 604/164.02
6,567,101 B1 5/2003 Thomas
6,589,262 B1 7/2003 Honebrink et al.
6,595,955 B2 7/2003 Ferguson et al.
6,602,240 B2 8/2003 Hermann et al.
6,607,353 B2 8/2003 Masutani
6,607,511 B2 8/2003 Halseth et al.
6,626,868 B1 9/2003 Prestidge et al.
6,641,564 B1 11/2003 Kraus
6,692,462 B2 2/2004 Mackenzie et al.
6,692,482 B2 2/2004 Heller et al.
6,695,816 B2 2/2004 Cassidy
6,714,809 B2 3/2004 Lee et al.
6,719,772 B2 4/2004 Trask et al.
6,726,659 B1 * 4/2004 Stocking et al. ..... 604/164.09
6,749,588 B1 6/2004 Howell et al.
6,786,875 B2 9/2004 Barker et al.
6,796,962 B2 9/2004 Ferguson et al.
6,808,520 B1 10/2004 Fourkas et al.
6,836,687 B2 12/2004 Kelley
6,902,546 B2 6/2005 Ferguson
6,905,481 B2 6/2005 Sirimanne
6,940,092 B2 9/2005 Yoshida et al.
6,972,002 B2 12/2005 Thorne
6,994,693 B2 2/2006 Tal
7,001,396 B2 2/2006 Glazier et al.
7,004,927 B2 2/2006 Ferguson et al.
7,025,746 B2 4/2006 Tal
7,109,967 B2 9/2006 Hioki et al.
7,125,396 B2 10/2006 Leinsing et al.
7,179,244 B2 2/2007 Smith et al.
7,182,755 B2 2/2007 Tal
7,192,433 B2 3/2007 Osypka et al.
7,196,689 B2 3/2007 Moriyama
7,226,434 B2 6/2007 Carlyon et al.
7,270,649 B2 9/2007 Fitzgerald
7,455,660 B2 11/2008 Schweikert et al.
7,458,954 B2 12/2008 Ferguson et al.
7,500,965 B2 3/2009 Menzi et al.
7,503,596 B2 3/2009 Rome et al.
7,556,617 B2 7/2009 Voorhees, Jr. et al.
7,611,485 B2 11/2009 Ferguson
7,614,123 B2 11/2009 Schweikert
7,618,395 B2 11/2009 Ferguson
7,670,316 B2 3/2010 Windheuser et al.
7,682,339 B2 * 3/2010 Fujii ..... 604/164.08
7,722,567 B2 5/2010 Tal
7,827,656 B2 11/2010 Schweikert
7,833,202 B2 11/2010 Suzuki
7,922,696 B2 4/2011 Tal et al.
8,021,338 B2 9/2011 Adams
8,070,750 B2 12/2011 Wenstrom, Jr. et al.
8,105,286 B2 1/2012 Anderson et al.
8,192,402 B2 6/2012 Anderson et al.
8,202,251 B2 6/2012 Bierman et al.
8,211,087 B2 7/2012 Carter et al.
8,377,006 B2 2/2013 Tal et al.
8,545,533 B2 10/2013 Spenser et al.
8,628,497 B2 1/2014 Finnestad et al.
8,657,790 B2 2/2014 Tal et al.
8,672,888 B2 3/2014 Tal
8,721,546 B2 5/2014 Belson
8,728,035 B2 5/2014 Warring et al.
8,900,192 B2 12/2014 Anderson et al.
8,915,884 B2 12/2014 Tal et al.
8,956,327 B2 2/2015 Bierman et al.
8,986,227 B2 3/2015 Belson
9,162,037 B2 10/2015 Belson et al.
9,375,553 B2 6/2016 Chrisman
9,402,979 B2 8/2016 Alokaili et al.
9,675,784 B2 6/2017 Belson
9,757,540 B2 9/2017 Belson
9,764,117 B2 9/2017 Bierman
10,086,171 B2 10/2018 Belson
10,136,916 B2 11/2018 Bierman et al.
10,220,191 B2 3/2019 Belson et al.
10,441,752 B2 10/2019 Bierman et al.
2002/0010436 A1 1/2002 Becker et al.
2002/0072712 A1 6/2002 Nool et al.
2002/0087076 A1 7/2002 Meguro et al.
2003/0032927 A1 2/2003 Halseth et al.
2003/0060842 A1 3/2003 Chin et al.
2003/0088212 A1 5/2003 Tal
2003/0153874 A1 * 8/2003 Tal ..... 604/164.1
2003/0171718 A1 * 9/2003 DeLegge et al. ..... 604/164.01
2003/0199827 A1 10/2003 Thorne
2003/0216771 A1 11/2003 Osypka et al.
2004/0008191 A1 1/2004 Poupyrev et al.
2004/0034383 A1 2/2004 Belson
2004/0092879 A1 5/2004 Kraus et al.
2004/0102789 A1 5/2004 Baughman
2004/0167439 A1 8/2004 Sharrow
2004/0171988 A1 9/2004 Moretti
2004/0193112 A1 9/2004 Glazier et al.
2004/0199197 A1 10/2004 Eidenschink et al.
2004/0220499 A1 11/2004 Griego et al.
2004/0239687 A1 12/2004 Idesawa et al.
2005/0027263 A1 2/2005 Woehr et al.
2005/0090835 A1 4/2005 Deal et al.
2005/0113798 A1 5/2005 Slater et al.
2005/0143770 A1 6/2005 Carter et al.
2005/0245875 A1 11/2005 Restelli et al.
2006/0015071 A1 1/2006 Fitzgerald
2006/0129100 A1 6/2006 Tal
2006/0178635 A1 8/2006 Callaway
2006/0274036 A1 12/2006 Hoiki et al.
2007/0021685 A1 1/2007 Oepen et al.
2007/0060889 A1 3/2007 Adams
2007/0161908 A1 7/2007 Goldman et al.
2007/0270751 A1 11/2007 Stangenes et al.
2007/0282300 A1 12/2007 Attawia et al.
2008/0262430 A1 10/2008 Anderson et al.

(56) References Cited

U.S. PATENT DOCUMENTS

| | | | |
|---|---|---|---|
| 2008/0262431 | A1 | 10/2008 | Anderson et al. |
| 2008/0294111 | A1 | 11/2008 | Tal et al. |
| 2009/0149857 | A1 | 6/2009 | Culbert et al. |
| 2009/0163861 | A1 | 6/2009 | Carlyon |
| 2009/0221961 | A1 | 9/2009 | Tal et al. |
| 2009/0264867 | A1 | 10/2009 | Schweikert et al. |
| 2010/0010441 | A1 | 1/2010 | Belson |
| 2010/0069880 | A1 | 3/2010 | Grayzel et al. |
| 2010/0191189 | A1 | 7/2010 | Harding et al. |
| 2010/0256567 | A1 | 10/2010 | Smith |
| 2011/0009827 | A1 | 1/2011 | Bierman et al. |
| 2011/0021994 | A1 | 1/2011 | Anderson et al. |
| 2011/0046564 | A1 | 2/2011 | Zhong |
| 2011/0202006 | A1 | 8/2011 | Bierman et al. |
| 2011/0218496 | A1 | 9/2011 | Bierman |
| 2011/0270192 | A1 | 11/2011 | Anderson et al. |
| 2011/0276002 | A1 | 11/2011 | Bierman |
| 2012/0004665 | A1 | 1/2012 | Defossez et al. |
| 2012/0041371 | A1 | 2/2012 | Tal et al. |
| 2012/0065590 | A1 | 3/2012 | Bierman et al. |
| 2012/0130307 | A1 | 5/2012 | Pobitschka |
| 2012/0283640 | A1 | 11/2012 | Bierman et al. |
| 2012/0316500 | A1 | 12/2012 | Bierman et al. |
| 2013/0123704 | A1 | 5/2013 | Bierman et al. |
| 2014/0025036 | A1 | 1/2014 | Bierman et al. |
| 2014/0081210 | A1 | 3/2014 | Bierman et al. |
| 2015/0190168 | A1 | 7/2015 | Bierman et al. |
| 2015/0297868 | A1 | 10/2015 | Tal et al. |
| 2015/0351793 | A1 | 12/2015 | Bierman et al. |
| 2017/0291009 | A1 | 10/2017 | Sos |
| 2018/0001060 | A1 | 1/2018 | Bierman et al. |
| 2018/0296804 | A1 | 10/2018 | Bierman |
| 2019/0076166 | A1 | 3/2019 | Bierman |

FOREIGN PATENT DOCUMENTS

| | | | |
|---|---|---|---|
| DE | 8914941 | U1 | 9/1990 |
| DE | 20211804 | U1 | 1/2003 |
| EP | 0139091 | | 7/1984 |
| EP | 0129745 | A2 | 1/1985 |
| EP | 0139091 | A1 | 5/1985 |
| EP | 0161636 | | 11/1985 |
| EP | 0161636 | A2 | 11/1985 |
| EP | 0352928 | A1 | 1/1990 |
| EP | 0411605 | A1 | 2/1991 |
| EP | 0583144 | A1 | 2/1994 |
| EP | 0502714 | | 11/1995 |
| EP | 0502714 | B1 | 11/1995 |
| EP | 0730880 | A1 | 9/1996 |
| EP | 734739 | A2 | 10/1996 |
| EP | 0745409 | A1 | 12/1996 |
| EP | 0750916 | A2 | 1/1997 |
| EP | 0806221 | A2 | 11/1997 |
| EP | 1570793 | A2 | 9/2005 |
| EP | 1458437 | B1 | 3/2010 |
| FR | 2368968 | A1 | 5/1978 |
| JP | 53-51692 | | 5/1978 |
| JP | 06285172 | A | 10/1994 |
| JP | 07148270 | A | 6/1995 |
| JP | 08336593 | A | 12/1996 |
| JP | 11299897 | A | 11/1999 |
| JP | 2001190682 | A | 7/2001 |
| JP | 2003512903 | A | 4/2003 |
| JP | 2003154013 | A | 5/2003 |
| JP | 2003265615 | A | 9/2003 |
| JP | 2004500218 | A | 1/2004 |
| JP | 2004097843 | A | 4/2004 |
| JP | 2005514114 | A | 5/2005 |
| JP | 07-503172 | | 2/2007 |
| JP | 2007503172 | A | 2/2007 |
| JP | 2007209721 | A | 8/2007 |
| JP | 2010504295 | A | 2/2010 |
| JP | 2010510039 | A | 4/2010 |
| JP | 2016163667 | A | 9/2016 |
| KR | 20050027359 | | 3/2005 |
| KR | 20050027359 | A | 3/2005 |
| WO | WO 83/01575 | | 5/1983 |
| WO | WO-8301575 | A1 | 5/1983 |
| WO | WO-8807388 | A1 | 10/1988 |
| WO | WO-9218193 | A1 | 10/1992 |
| WO | WO-9311812 | A1 | 6/1993 |
| WO | WO-9312826 | A1 | 7/1993 |
| WO | WO-9412233 | A1 | 6/1994 |
| WO | WO-1997005912 | A2 | 2/1997 |
| WO | WO-9804189 | A1 | 2/1998 |
| WO | WO-98024494 | A1 | 6/1998 |
| WO | WO-9857685 | A1 | 12/1998 |
| WO | WO-0000104 | A1 | 1/2000 |
| WO | WO-2001/23028 | A1 | 4/2001 |
| WO | WO-01024865 | A1 | 4/2001 |
| WO | WO-01041860 | A1 | 6/2001 |
| WO | WO-0178595 | A1 | 10/2001 |
| WO | WO-2002/41932 | A2 | 5/2002 |
| WO | WO-0236179 | A2 | 5/2002 |
| WO | WO-2003/057272 | A2 | 7/2003 |
| WO | WO-06119503 | A1 | 11/2006 |
| WO | WO 2007/046850 | | 4/2007 |
| WO | WO-2007046850 | A2 | 4/2007 |
| WO | WO-08064332 | A2 | 5/2008 |
| WO | WO 2008/131289 | | 10/2008 |
| WO | WO-2008131289 | A2 | 10/2008 |
| WO | WO-2010048449 | A2 | 4/2010 |
| WO | WO-2010056906 | A2 | 5/2010 |
| WO | WO-2010083467 | A2 | 7/2010 |
| WO | WO 2010/132608 | | 11/2010 |
| WO | WO-2010132608 | A2 | 11/2010 |
| WO | WO-2012135761 | A1 | 10/2012 |
| WO | WO-2012162677 | A1 | 11/2012 |
| WO | WO-2013026045 | A1 | 2/2013 |
| WO | WO-13067518 | A1 | 5/2013 |

OTHER PUBLICATIONS

U.S. Appl. No. 14/524,978, filed Oct. 27, 2014, by Steven F. Bierman, et al.

U.S. Appl. No. 14/543,576, filed Nov. 17, 2014, now U.S. Pat. No. 9,764,117, issued on Sep. 19, 2017, by Steven F. Bierman, et al., Office Action dated Sep. 16, 2016; and Notice of Allowance dated May 15, 2017.

U.S. Appl. No. 15/703,026, filed Sep. 13, 2017, now U.S. Pat. No. 10,441,752, issued on Oct. 15, 2019, by Steven F. Bierman, et al., Notice of Allowance dated Aug. 6, 2019.

U.S. Appl. No. 13/185,358, filed Jul. 18, 2011, now U.S. Pat. No. 8,900,192, issued on Dec. 2, 2014, by Janelle Anderson, et al., Office Actions dated Jan. 7, 2013, Jun. 6, 2013, Nov. 26, 2013 and Apr. 14, 2014; and Notice of Allowance dated Jul. 28, 2014.

U.S. Appl. No. 12/106,119, filed Apr. 18, 2008, now U.S. Pat. No. 8,192,402, issued on Jun. 5, 2012, by Janelle Anderson, et al., Office Action dated Sep. 15, 2011; and Notice of Allowance dated Feb. 8, 2012.

U.S. Appl. No. 13/466,933, filed May 8, 2012, by Janelle Anderson, et al.

U.S. Appl. No. 12/019,598, filed Jan. 24, 2008, now U.S. Pat. No. 7,922,696, issued on Apr. 12, 2011, by Michael Tal, et al., Office Action dated Jun. 25, 2009; and Notices of Allowance dated Apr. 16, 2010, Sep. 27, 2010, and Jan. 24, 2011.

U.S. Appl. No. 13/084,440, filed Apr. 11, 2011, now U.S. Pat. No. 8,377,006, issued on Feb. 19, 2013, by Michael Tal, et al., Office Action dated Dec. 21, 2011; and Notice of Allowance dated Oct. 15, 2012.

U.S. Appl. No. 13/747,335, filed Jan. 22, 2013, now U.S. Pat. No. 8,915,884, issued on Dec. 23, 2014, by Michael Tal, et al., Office Action dated Oct. 25, 2013; and Notices of Allowance dated Mar. 3, 2014 and Jul. 23, 2014.

U.S. Appl. No. 14/578,085, filed Dec. 19, 2014, by Michael Tal, et al., Office Actions dated Sep. 1, 2016 and Jul. 10, 2017.

U.S. Appl. No. 16/246,489, filed Jan. 12, 2019, by Steven F. Bierman, et al.

U.S. Appl. No. 16/246,490, filed Jan. 12, 2019, by Steven F. Bierman, et al.

(56) References Cited

OTHER PUBLICATIONS

U.S. Appl. No. 16/738,316, filed Jan. 9, 2020, by Michael Tal, et al., Office Action dated Feb. 18, 2020.
U.S. Appl. No. 16/738,310, filed Jan. 9, 2020, by Michael Tal, et al., Office Action dated Feb. 18, 2020.
Examination Report for European Application No. 02806219.8-2310 dated May 16, 2008.
Examination Report for European Application No. 02806219.8-2310 dated Sep. 18, 2007.
International Search Report for PCT Application No. PCT/US/2002/041371, dated Oct. 2, 2003.
International Search Report for PCT Application No. PCT/US/2006/011624, dated Oct. 17, 2007.
International Search Report for PCT Application No. PCT/US/2008/051950, dated Oct. 22, 2008.
International Search Report PCT-US2009-037198 dated Jun. 15, 2009.
Results of Partial International Search for PCT Application No. PCT/US/2008/060914, dated Oct. 29, 2008.
Results of Partial International Search for PCT Application No. PCT/US/2008/060930, dated Oct. 29, 2008.
A photograph of various access devices, Jul. 20, 2011.
A photograph of various access devices, Mar. 1, 2007.
International Search Report and Written Opinion in Application No. PCT/US2019/019640 dated Jun. 5, 2019 30 pages.
Office Action from EP 08746350.1-2310 dated Jun. 17, 2011.
Office Action in EP 08746365.9-2310 dated Jul. 12, 2011.
Photograph of various access devices.
Photos of a peripheral emergency infusion device Applicant believes to be produced by Arrow International Inc.
Photos of a peripheral emergency infusion device Applicant believes to be produced by Arrow International Inc., Jul. 20, 2011.
Photos of a splittable catheter design.
Photos of a splittable catheter design, Jul. 20, 2011.
Photos of an infusion device Applicant believes to be produced by B. Braun Medical Inc.
Photos of an infusion device Applicant believes to be produced by B. Braun Medical Inc., Jul. 20, 2011.
Photos of an infusion device Applicant believes to be produced by B. Braun Medical Inc., Mar. 1, 2007.
Results of Preliminary Report of PCT/US2008/060930, filed on Apr. 18, 2008, mailed on Oct. 29, 2009.
Results of Preliminary Report of PCT/US2008/060914 filed Apr. 18, 2008, mailed Oct. 20, 2009.
U.S. Department of Health and Human Services, "Medical Devices with Sharps Injury Prevention Features," Guidance for Industry and FDA Staff in 20 pages. Issued on Aug. 9, 2005.
A photograph of various access devices.
Arrow Trauma Products No. TRM-C 12/00 11M, Arrow International, dated 2000.

* cited by examiner

"Amended"

ACCESS DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a continuation of U.S. patent application Ser. No. 12/019,598, filed on Jan. 24, 2008 and entitled "ACCESS DEVICE," issued as U.S. Pat. No. 7,922,696 on Apr. 12, 2011, which claims the benefit under 35 U.S.C. §119(e) to U.S. Provisional Patent Application Ser. No. 60/886,443, filed Jan. 24, 2007, the entire contents of each hereby incorporated by reference.

BACKGROUND OF THE INVENTION

1. Field of the Invention

This invention is generally directed to access devices for introducing and delivering a catheter cannula or sheath into an artery, vein, vessel, body cavity, or drainage site.

2. Description of the Related Art

A preferred non-surgical method for inserting a catheter or vascular sheath into a blood vessel involves the use of the Seldinger technique, which includes an access needle that is inserted into a patient's blood vessel. A guidewire is inserted through the needle and into the vessel. The needle is removed, and a dilator and sheath combination are then inserted over the guidewire. The dilator and sheath combination is then inserted a short distance through the tissue into the vessel, after which the dilator and guidewire are removed and discarded. The catheter may then be inserted through the sheath into the vessel to a desired location.

A number of vascular access devices are known. U.S. Pat. Nos. 4,241,019, 4,289,450, 4,756,230, 4,978,334, 5,124,544, 5,424,410, 5,312,355, 5,212,052, 5,558,132, 5,885,217, 6,120,460, 6,179,823, and 6,210,332 disclose examples of such devices. None of these devices, however, has the ease and safety of use that physicians and other healthcare providers would prefer and, thus, there is a need for an easier-to-use and safer vascular access device, especially one that would clearly indicate when a blood vessel has been punctured.

SUMMARY OF THE INVENTION

The present invention involves several features for an access device useful for the delivery of a catheter or sheath into a space within a patient's body, such as, for example, a blood vessel or drainage site. Without limiting the scope of this invention, its more prominent features will be discussed briefly. After considering this discussion, and particularly after reading the Detailed Description of the Preferred Embodiments section below in combination with this section, one will understand how the features and aspects of this invention provide several advantages over prior access devices.

One aspect of the present invention is an access device for placing a medical article within a body space. The device has a needle section that includes an elongated body and a needle hub. The elongated body has distal and proximal ends. The distal end is configured for insertion into a patient's body. The proximal end is coupled with the needle hub. The device further includes a dilator portion including a dilator and a dilator hub. The dilator is coaxially disposed and slideable over the elongated body of the needle section with the dilator hub being disposed distal of the needle hub. The device further includes a sheath section that has a sheath and a sheath hub. The sheath is coaxially disposed and slideable over the dilator with the sheath hub being disposed distal of the dilator hub. The device further includes a first locking mechanism operably disposed between the needle hub and the dilator hub to inhibit at least unintentional axial movement between the needle section and the dilator portion when the first locking mechanism is engaged and a second locking mechanism operably disposed between the dilator hub and the sheath hub to inhibit at least unintentional axial movement between the dilator portion and the sheath section when the second locking mechanism is engaged. Each of said first and second locking mechanisms is configured to be engaged by moving the respective hubs in a non-axial manner relative to each other. The first locking mechanism is configured to move in a manner different from the manner in which the second locking mechanism is engaged.

Another aspect of the invention is an access device for placing a medical article within a body space. The device includes a needle section including an elongated needle body with a sharp distal tip and a needle hub from which the needle body extends. The device further includes a dilator portion that includes a dilator and a dilator hub. The dilator is coaxially disposed and slideable over the needle body with the dilator hub being disposed distal of the needle hub. The device further includes a sheath section that includes a sheath and a sheath hub. The sheath is coaxially disposed and slideable over the dilator with the sheath hub being disposed distal of the dilator hub. The device further includes a locking mechanism disposed within the dilator and selectively operating between the needle body and the dilator. The locking mechanism is configured to arrest axial movement of the needle body at least in the distal direction once the distal tip of the needle body is drawn into the dilator portion to sheath the distal tip.

Yet another aspect of the invention is an access device for placing a medical article within a body space. The device includes a dilator hub that has a passageway configured to receive an elongated needle. The needle has at least one side receptacle. The device further includes one or more fingers or tangs disposed in the dilator hub and configured to engage with the at least one side receptacle at least when the needle is retracted through the passageway.

Additionally, a releasable interlock can be provided in some embodiments to inhibit relative rotational movement between the needle section and the dilator section, at least when the needle is inserted into a patient. By inhibiting such relative rotational movement, communicating side openings in the needle and the dilator can be held in alignment to provide a simplified passageway through which the blood or fluid may flow. Thus, when the needle enters a blood vessel or drainage site in the patient, blood or other body fluid quickly flows into the passageway. The resulting blood or fluid flash is visible through the sheath section (or catheter) to indicate that the needle tip has entered the vessel or drainage site.

For example, but without limitation, the dilator portion or section can comprise, in some embodiments, a dilator hub and dilator having one or more side openings. The dilator hub may have a luer connection and a releasable locking mechanism. The releasable locking mechanism can be configured to releasably engage and secure the dilator section to another part, such as the needle hub. When the needle hub and the dilator hub are releasably locked to prevent rotation therebetween, one or more of the side openings in the dilator are aligned with one or more side openings in the needle. The locking mechanism can also be configured to inhibit unintentional relative axial movement between the needle and the dilator.

The sheath section preferably, but not necessarily, includes a sheath and sheath hub. The sheath may be made partially or completely from a clear, translucent, semi-opaque, or transparent material. Such transparent, translucent, semi-opaque and clear materials allow a clinician the ability to see when blood or other body fluids flows into the needle, through the needle side opening(s), through the side dilator opening(s), and into the viewing space between the dilator and sheath.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the invention disclosed herein are described below with reference to the drawings of preferred embodiments, which are intended to illustrate and not to limit the invention.

FIG. 8A illustrates the locking mechanism in an unlocked state.

FIG. 9A illustrates the locking mechanism in an unlocked state.

FIG. 10A illustrates the locking mechanism in an unlocked state.

DETAILED DESCRIPTION OF THE PREFERRED EMBODIMENTS

The present disclosure provides an access device for the delivery of a catheter or sheath to a blood vessel or drainage site. FIG. 1 illustrates an access device 102 that is configured to be inserted into a blood vessel in accordance with a preferred embodiment of the present invention. While the access device is described below in this context (i.e., for vascular access), the access device also can be used to access and place a catheter or sheath into other locations within a patient's body (e.g., for draining an abscess) and for other purposes.

Figure 1A:
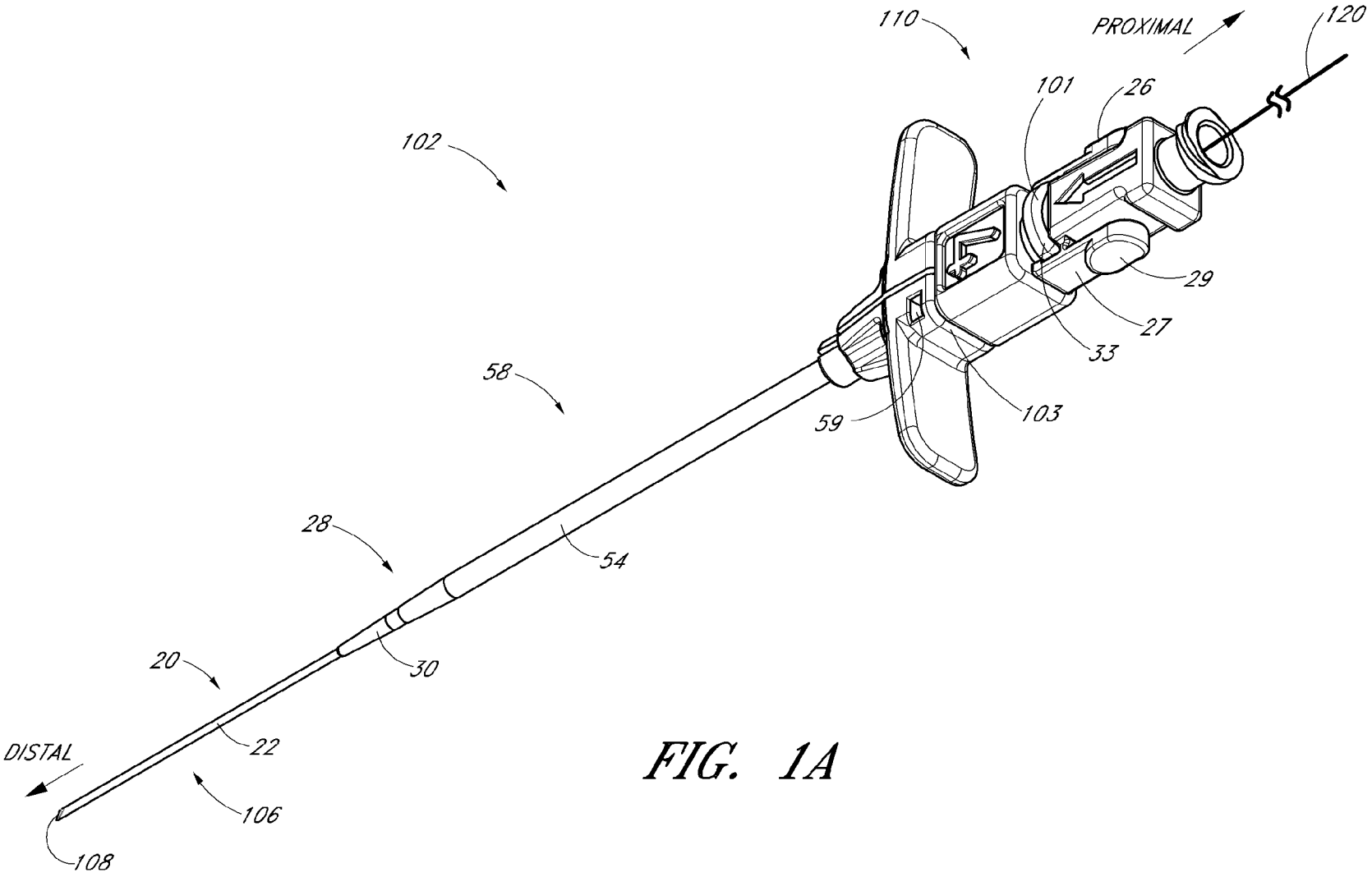
FIG. 1A is a perspective view of a preferred embodiment of an access device configured in accordance with the present invention.

FIG. 1A is a perspective view of a preferred embodiment of an access device 102. The access device 102 comprises a needle section 20, a dilator portion 28, a sheath section (e.g., catheter or cannula) 58, and a guidewire 120. In preferred embodiments, the dilator portion 28 is coaxially mounted on the needle section 20, and the sheath section 58 is coaxially mounted on the dilator portion 28. The needle section 20 comprises a needle 22 and a needle hub 21. The needle hub 21 is disposed on a proximal end of the needle 22. The dilator portion 28 comprises a dilator 30 and a dilator hub 32. The dilator hub 32 is disposed on the proximal end of the dilator 30. The sheath section 58 comprises a sheath 54 and a sheath hub 53. The sheath hub 53 is disposed on the proximal end of the sheath 54.

Figure 1B:
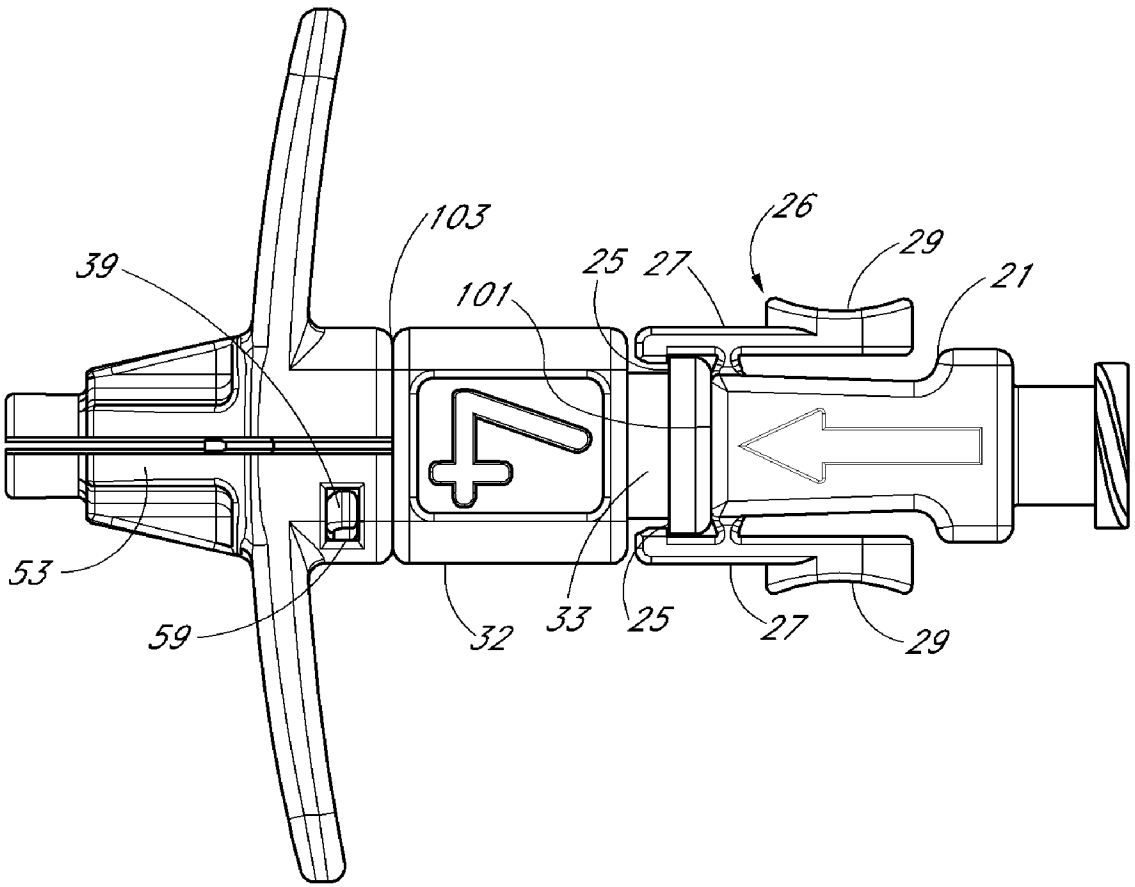
FIG. 1B is an enlarged plan view of a needle hub, a dilator hub, and a sheath hub of the access device illustrated in FIG. 1A, shown in an assembled state.

FIG. 1B is an enlarged plan view of the needle hub 21, the dilator hub 32, and the sheath hub 53 of the access device illustrated in FIG. 1A, shown in an assembled state. The needle hub 21, the dilator hub 32, and the sheath hub 53 include structures that releasably interlock the hubs so as to provide a structural and fluid connection between the needle section 20, the dilator portion 28, and the sheath section 58.

Figure 1C:
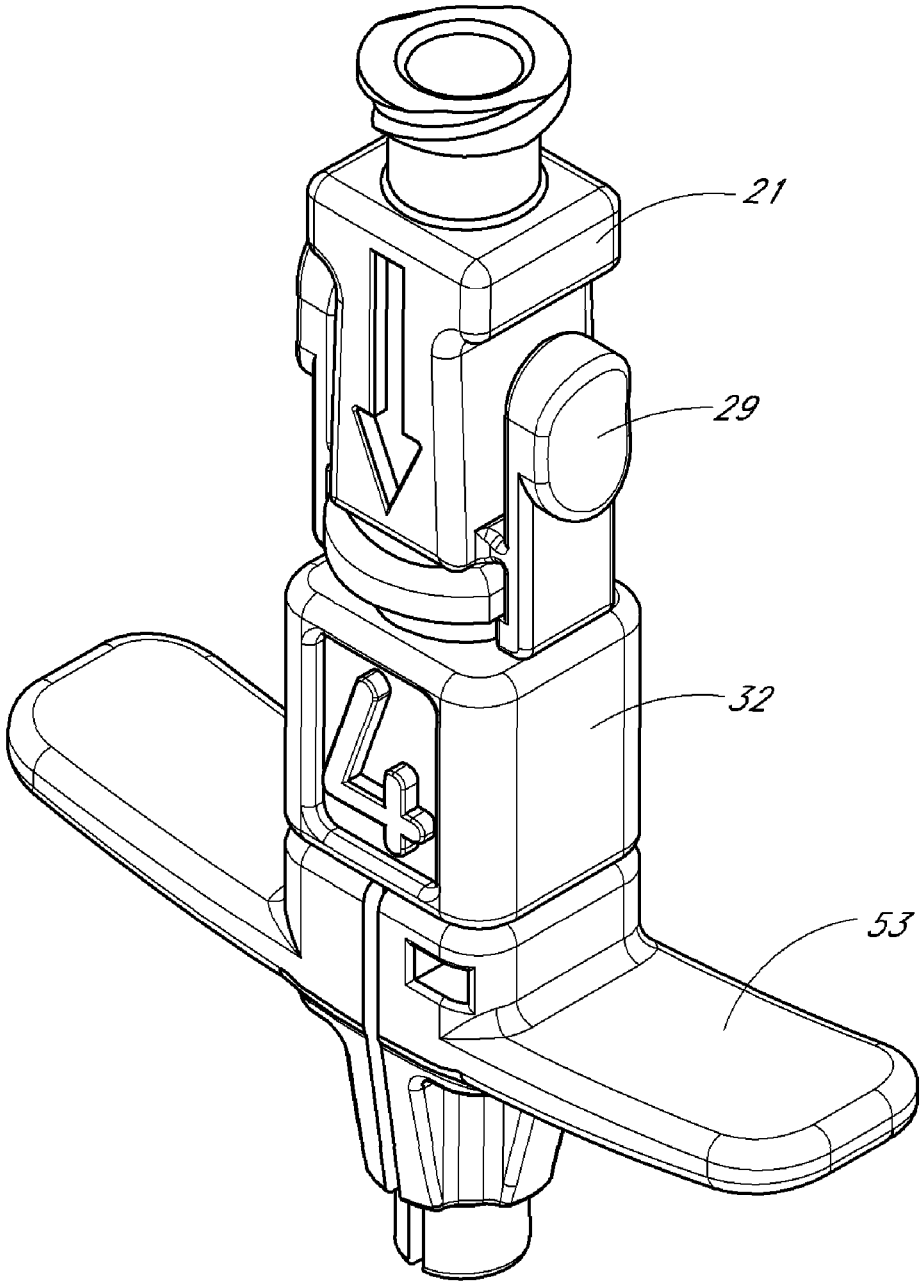
FIG. 1C is a perspective view of the assembly of the needle hub, dilator hub and sheath hub illustrated in FIG. 1B.

FIG. 1C is a perspective view of the assembly of the needle hub 21, dilator hub 32 and sheath hub 53 illustrated in FIG. 1B. With reference to FIGS. 1A and 1B, the needle section 20, dilator portion 28, and sheath section 58 are interlocked at the proximal end 110 of the access device 102. In some embodiments, the releasable interlock between the needle section 20, dilator portion 28, and sheath section 58 is a tandem interlock where the dilator portion 28 is locked to the needle section 20 at interface 101 and the sheath section 58 is locked to the dilator portion 28 at interface 103. In additional to a structural connection, the interlocks provide a fluidic connection through the access device 102.

Preferably, the needle section 20 locks to the dilator portion 28 via a lock mechanism 26. The lock mechanism 26 may comprise an engaging mechanism such as hinged clips 27 with actuator sides 29. The hinged clips 27 may releasably engage and secure to corresponding catches 25 on the dilator portion 28. In some embodiments, the clip sides 29 engage and secure the dilator portion 28 by clipping to the outer lip of a luer connection 33 on the dilator portion 28. Although hinged clips 27 are shown, the lock member 26 may comprise any suitable engaging mechanism known in the art. In the illustrated embodiment, as best seen in FIG. 3B, the portions of the outer lip onto which the hinge clips 27 engage are flats to inhibit rotation of the needle hub 21 relative to the dilator hub 32 after a certain degree of relative rotation (e.g., 180 degrees) between the needle hub 21 and the dilator hub 32.

Similarly, the sheath section 58 is secured to the dilator portion 28 through a lock member 59. The sheath section 58 may, preferably, comprise a twist lock member 59 so that the user may releasably engage and secure the dilator portion 28 to the sheath section 58. In some preferred embodiments, the dilator portion 28 comprises teeth or prongs that are configured to mate or attach to corresponding areas on the sheath section 58. Preferably, the needle 20, dilator 28 and sheath 58 are releasably locked so that a physician or user may remove sections or portions of the access device as needed for treatment.

Figure 2A:
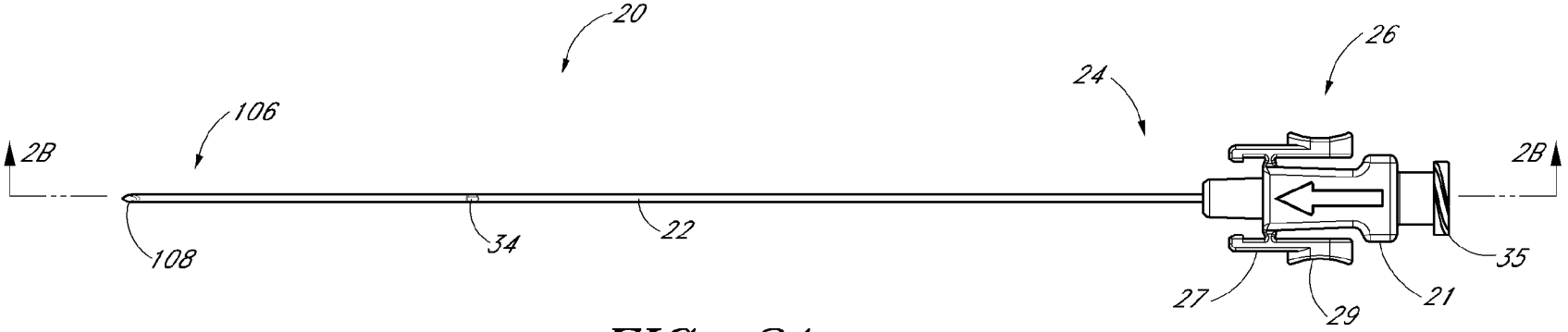
FIG. 2A is side view of a needle section of the embodiment depicted in FIG. 1A.
Figure 2B:
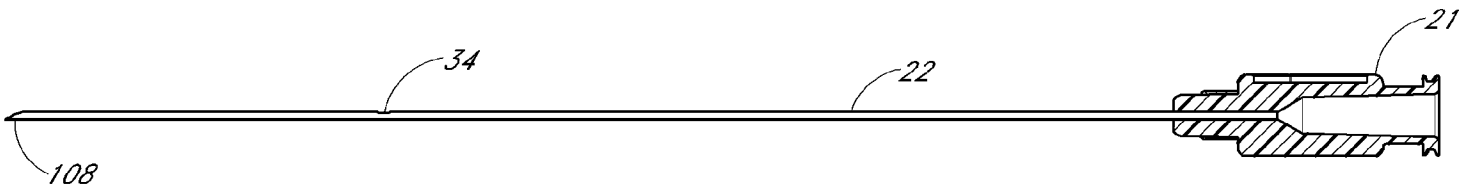
FIG. 2B is a cross-sectional view of the needle section of the embodiment depicted in FIG. 2A taken along line A-A.

FIG. 2A is side view of the needle section 20 of the embodiment depicted in FIG. 1A. FIG. 2B is a cross-sectional view of the needle section 20 depicted in FIG. 2A taken along line A-A. As shown in both FIGS. 2A and 2B, the needle section 20 has a needle 22, distal portion 106, and proximal portion 24. Preferably, the proximal portion 24 has the needle hub 21 and the lock member 26. In addition, the needle 22 may have a bevel tip 108 disposed on the distal portion 106. The needle 22 may further comprise one or more side openings 34.

Figure 2C:
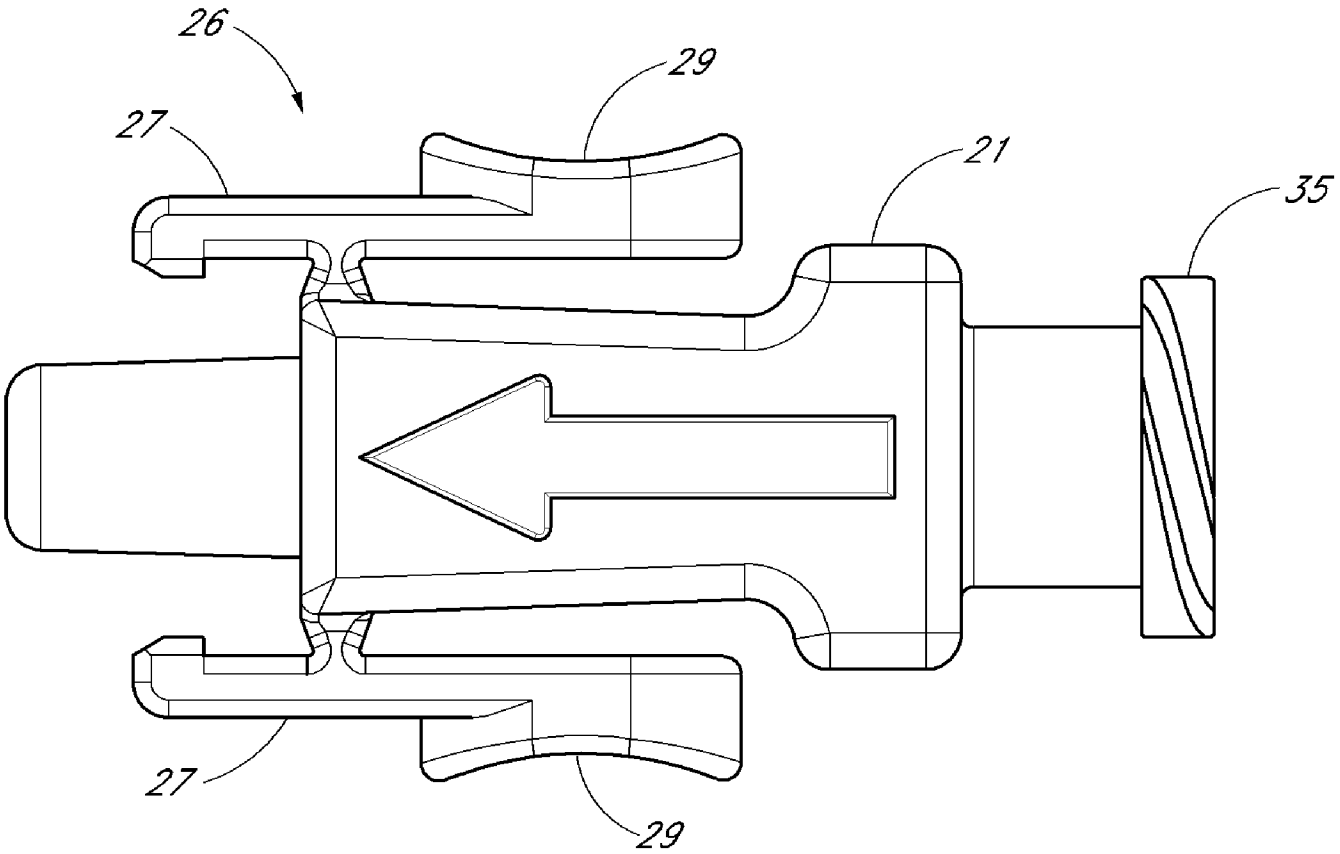
FIG. 2C is an enlarged plan view of the needle hub of the needle section of FIG. 2B.

FIG. 2C is an enlarged plan view of the needle hub 21 of the needle section 20 of FIG. 2B. As most clearly shown in FIG. 2C, the needle hub 21 may also have a luer connection 35 at the proximal portion 24 of the needle 20. This allows the physician or healthcare provider, for example, to introduce a guidewire 120 through the hollow portion of the luer connection 35, through the needle 22, and into a punctured vessel. Additionally, a physician or healthcare provider may also attach a syringe to the luer connection 35 to perform other procedures as desired.

As discussed above, in preferred embodiments, the needle hub 21 comprises the lock member 26. The lock member 26 may be configured to lock or secure another part such as, for example, the dilator portion 28 or the sheath section 58, to the needle section 20. As shown most clearly in FIG. 2C, the lock member 26 can comprise an engaging mechanism such as a pair of hinged clips 27, although other types of locking mechanisms comprising tabs and/or slots can also be used. Preferably, the clip sides 29 of the hinged clips 27 can engage a lipped surface such as the outer lip of a luer connection 33, shown in FIG. 1A. Once engaged, the clip sides 29 prevent the locked part from undesired slipping or releasing. In certain embodiments, the clips 27 are hinged to provide a bias towards the center of the needle hub 21. Preferably, the bias prevents the secured part from slipping or disengaging from the hinged clips 27. More preferably, the bias of the hinged clips 27 can be overcome by simultaneously applying pressure on the sides 29 of the clips 27 to release, for example, the luer connection 33 from the needle hub 21. To apply the appropriate releasing pressure, a physician or healthcare provider may, for example, place an index finger and thumb on the sides 29 of the hinged clips 27 and apply squeezing pressure to overcome the hinge bias. The hinged clips 27 will, preferably, release only when sufficient releasing pressure is applied to both clip sides 29.

As shown most clearly in FIG. 2A, the needle proximal portion 24 may have color coding, words, or other indicia, such as a pivot or notch, to indicate to the operator the position of the bevel tip 108 relative to the dilator 28 or the sheath section 58. For example, the arrow embedded into the needle hub 21 indicates the bevel up position of the needle 22 and may further indicate to the healthcare provider the proper way to use the device. Also, there may be a mechanical fit between the dilator 28 and the needle 22 so that the physician or healthcare provider would sense by feel or sound (e.g., by a click) when the needle 22 has been rotated to change the position of the bevel tip 108.

Figure 3A:
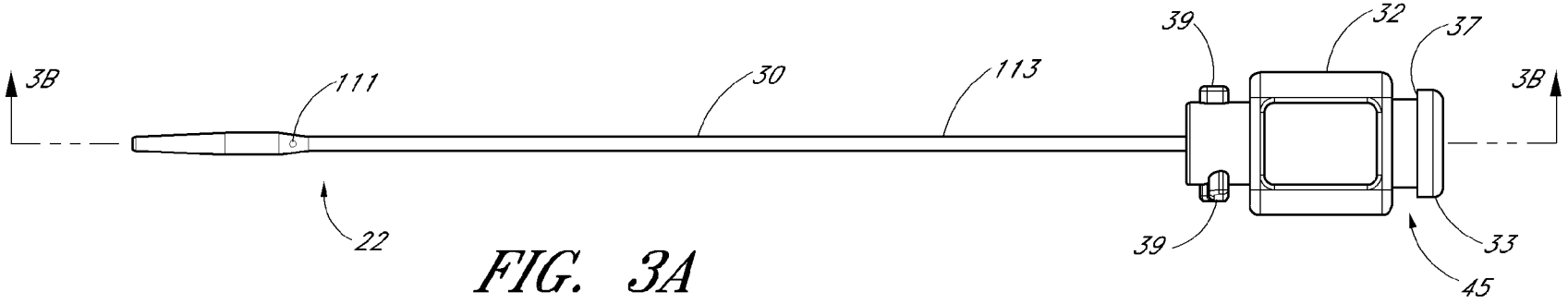
FIG. 3A is a side view of the dilator portion of the embodiment depicted in FIG. 1A.
Figure 3B:
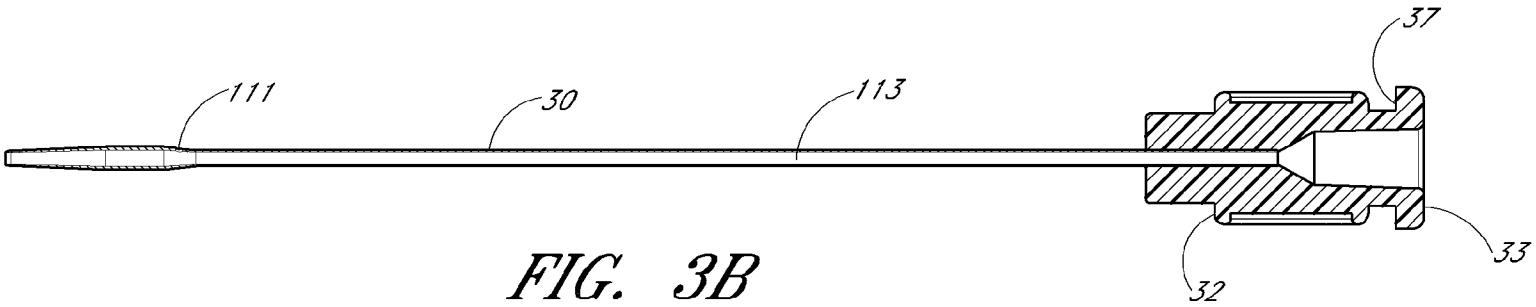
FIG. 3B is a proximal end view of the dilator portion of FIG. 3A.
Figure 3C:
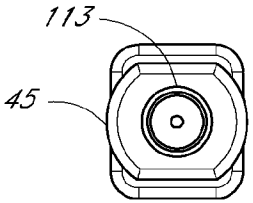
FIG. 3C is a cross-sectional view of the dilator portion of the embodiment depicted in FIG. 3A, taken along line B-B.

FIG. 3A is a side view of the dilator portion 28 of the embodiment depicted in FIG. 1A. FIG. 3B is a proximal end view of the dilator portion 28 of FIG. 3A. FIG. 3C is a cross-sectional view of the dilator portion 28 of the embodiment depicted in FIG. 3A, taken along line B-B. As shown, the dilator portion 28 may comprise the dilator 30 and the dilator hub 32. The dilator 30 may further comprise one or more side openings 111. The dilator hub 32 preferably comprises a luer connection 33 with an outer lip 37. In some embodiments, the outer lip 37 can be configured to engage to the lock member 26 on the needle section 20 illustrated in FIG. 2C.

Additionally, the dilator 30 may be coaxially mounted to the needle 22 by slipping a hollow section 113 of the dilator 30 over the needle 22 and releasably securing the dilator hub 32 to the needle hub 21. Preferably, the proximal end 45 of the dilator hub 32 is configured to mechanically fit and interlock with the needle lock member 26 to inhibit at least some rotational and axial motion. More preferably, the dilator 30 is releasably mounted to the needle 22 so that the dilator 30 can be mounted and released, or vice versa, from a coaxial position relative to the needle 22.

Figure 3D:
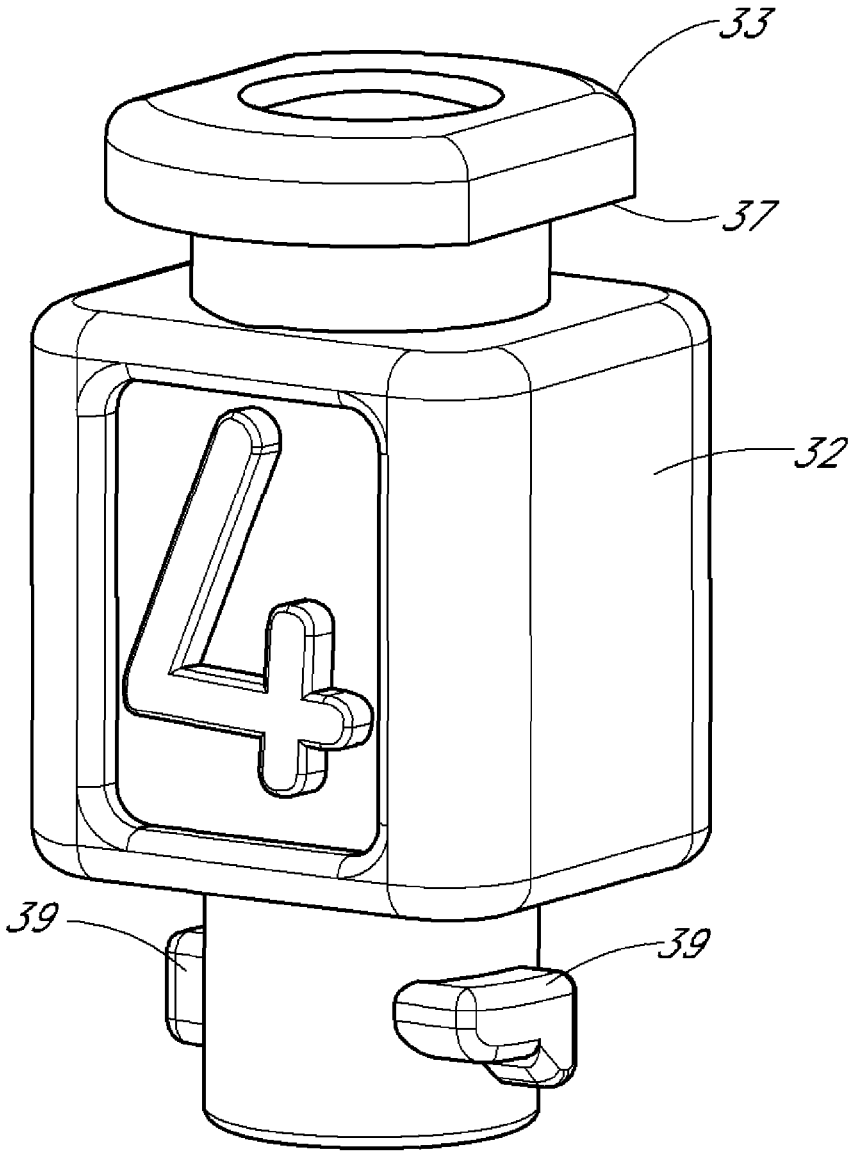
FIG. 3D is an enlarged perspective view of the dilator hub of the dilator portion of FIG. 3A.

FIG. 3D is an enlarged perspective view of the dilator hub 32 of the dilator portion 28 of FIG. 3A. As is most clearly illustrated in FIG. 3D, the dilator hub 32 may further comprise a locking mechanism 39. The locking mechanism 39 comprises one or more posts, teeth, or prongs projecting from the dilator hub 32. The locking mechanism 39, which may be in the form of teeth, can be configured to mate or attach to corresponding receiving areas disposed on another part such as the sheath section 58 or the needle hub 21. This locking mechanism 39 will be explained in greater detail in the following section.

Figure 4A:
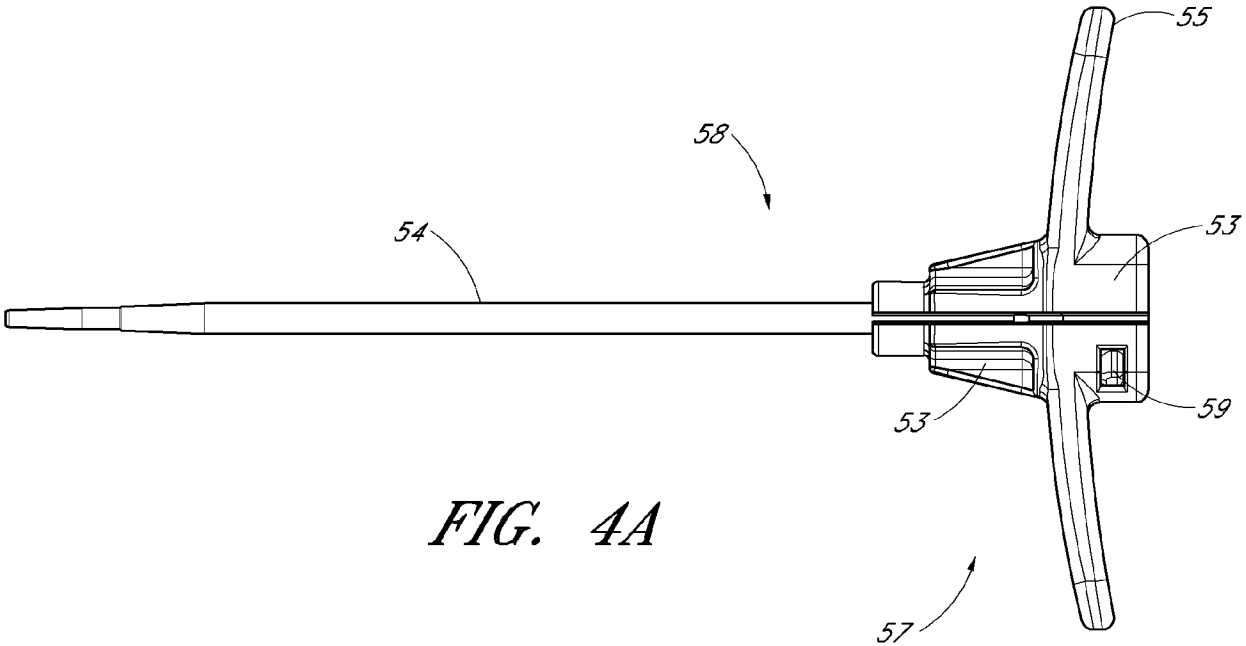
FIG. 4A is a side view of a sheath section of the embodiment from FIG. 1A.
Figure 4B:
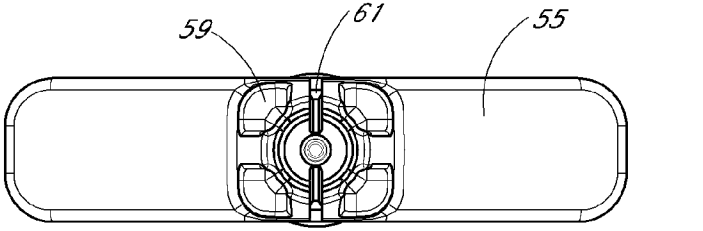
FIG. 4B is a proximal end view of the sheath section of FIG. 4A.

FIG. 4A is a side view of the sheath section 58 of the embodiment from FIG. 1A. FIG. 4B is a proximal end view of the sheath section 58 of FIG. 4A. In preferred embodiments, the sheath section 58 comprises a sheath 54 and a sheath hub 53. The sheath 54 may also be made partially or completely from clear, translucent, transparent, or semi-opaque material. The sheath hub 53 may further comprise winged ends 55 and a lock member 59.

Figure 4C:
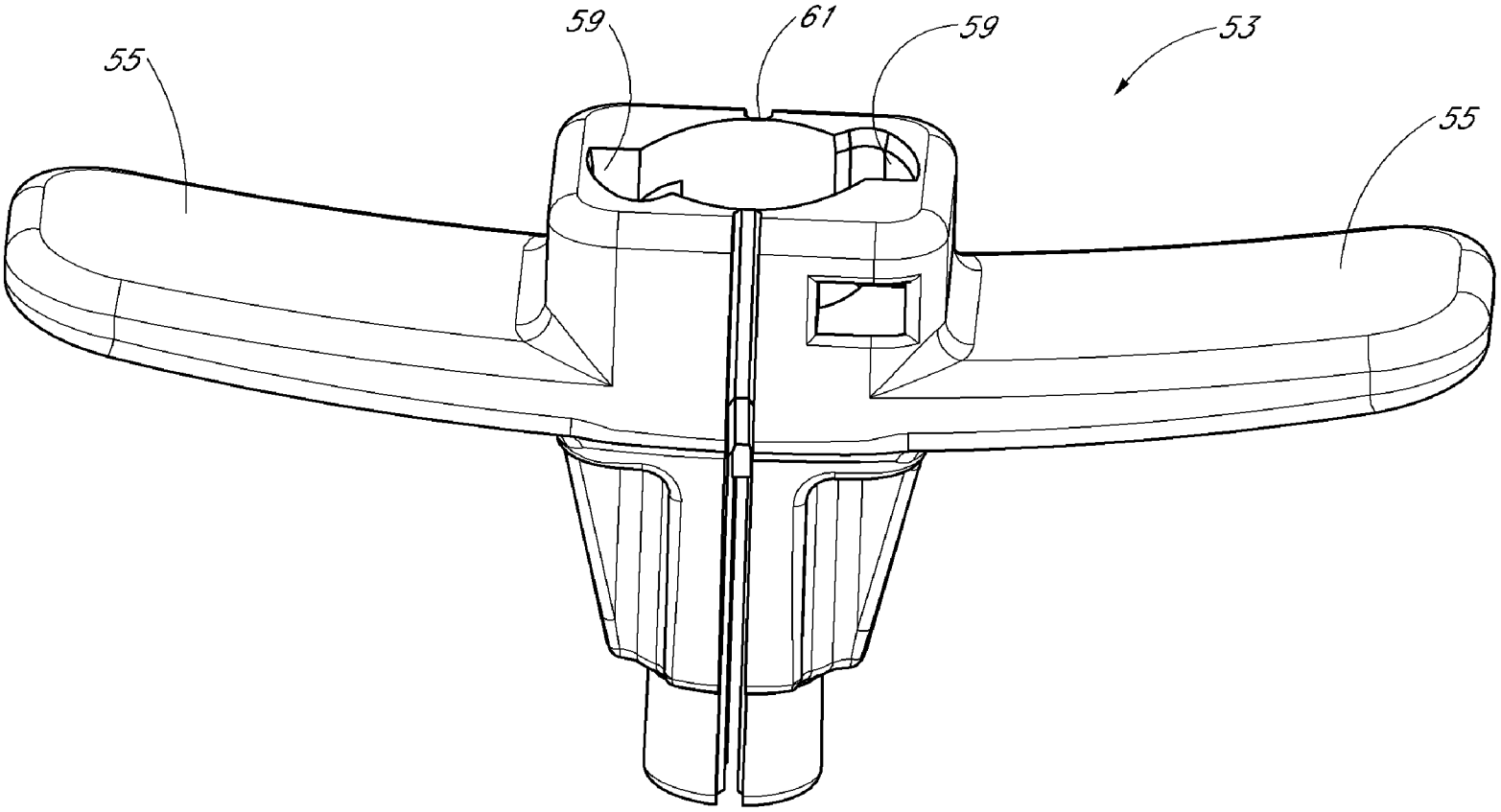
FIG. 4C is an enlarged perspective view of the sheath hub of the sheath section of FIG. 4A.

FIG. 4C is an enlarged perspective view of the sheath hub 53 of the sheath section 58 of FIG. 4A. Preferably, the locking member 59 may comprise a locking or attaching structure that mates or engages with a corresponding structure. As most clearly shown in FIGS. 4B and 4C, the locking member 59 may comprise indentations, bumps, or grooves designed to engage and secure the locking mechanism or teeth 39 on the dilator hub 32 described above with reference to FIG. 3D.

The sheath hub 53, as best seen in FIGS. 4B and 4C, preferably is designed so that the locking mechanism or teeth 39 of the dilator hub 32 can enter the sheath hub 53 substantially unobstructed. However, in use, once the sheath hub 53 is placed at a desired location over the dilator 30, the physician or healthcare provider can twist the sheath hub 53 and disengage or engage the locking member 59. The locking member 59 can be, for example, a protruding bump, dent, etc., that creates a mechanical fit so that the dilator hub 32 and the sheath hub 53 are releasably interlocked. In the illustrated embodiment, the locking member 59 of the sheath hub 53 comprises a pair of axial arranged grooves which extend from a distal side of the sheath hub 53 and terminate at a protruding bump, dent, etc. Preferably, the locked position can be disengaged by twisting the dilator hub 32 relative to the sheath hub 53. Additionally, the sheath hub may comprise wings 55 or handle structures to allow for easy release and removal of the sheath 54 from other parts of the access device 102.

In some applications, the wings 55 are sized to provide the healthcare provider with leverage for breaking apart the sheath hub 53. For example, the sheath hub 53 may comprise a thin membrane 61 connecting the halves of the sheath hub 53. The membrane 61 is sized to keep the halves of the sheath hub 53 together until the healthcare provider decides to remove the sheath hub 53 from the access device. The healthcare provider manipulates the wings 55 to break the membrane 61 and separate the sheath hub 53 into removable halves.

Figure 5:
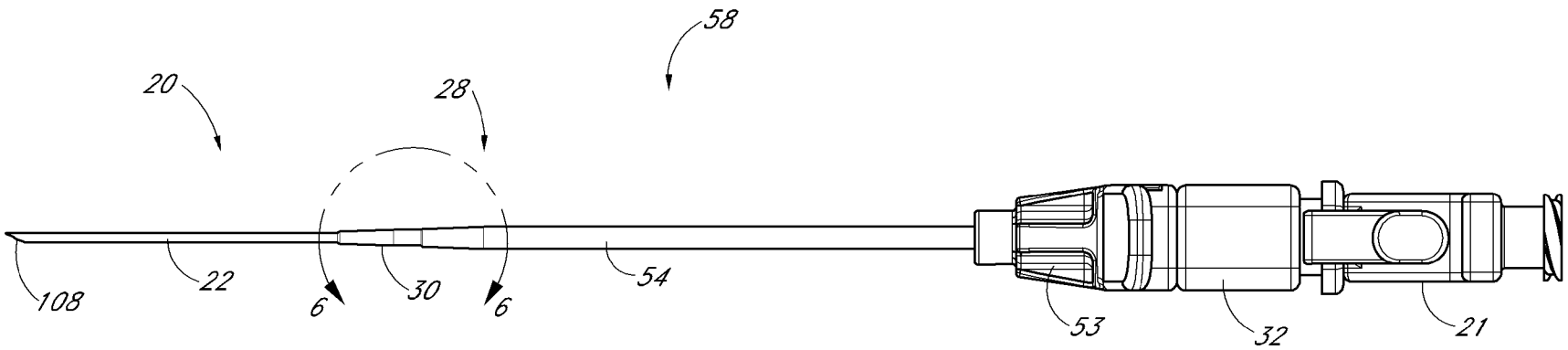
FIG. 5 is a side view of the access device of FIG. 1A.

FIG. 5 is a side view of the access device of FIG. 1A in which the needle section 20, dilator portion 28, and sheath section 58 are interlocked together. In the assembly, as noted above the needle section 20, dilator portion 28 and sheath section 58 are coaxially disposed about a common longitudinal axis and form a central fluid connection.

Figure 6:
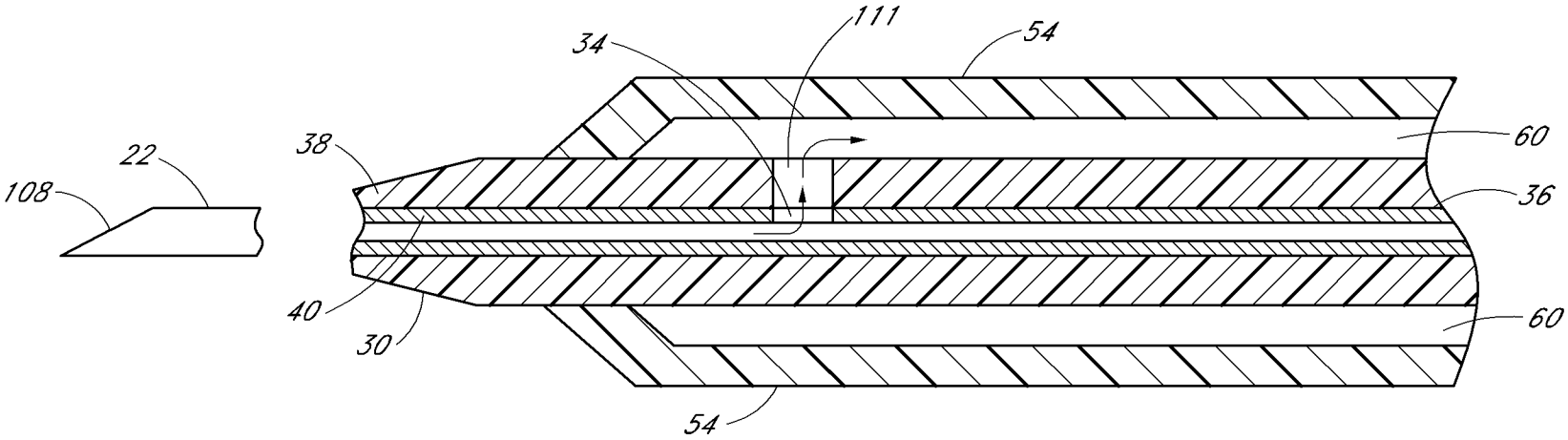
FIG. 6 is an enlarged cross-sectional view of a portion of the embodiment illustrated in FIG. 5 which is circled by line C-C.

FIG. 6 is an enlarged cross-sectional view of a portion of the embodiment illustrated in FIG. 5 which is circled by line C-C. As noted above, the needle 22, preferably, comprises one or more side openings 34 in its side wall. Additionally, the dilator may comprise one or more side openings 111. FIG. 6, however, illustrates the alignment between only one set of corresponding side openings. Other sets of side openings can also be aligned or be misaligned depending upon the relative orientations of the needle and the dilator.

Preferably the dilator 30 may be coaxially positioned to minimize the annular space 36 between the needle 22 and the dilator 30. The inner surface 38 of the dilator 30 need not, though it can, lie directly against the outer-surface 40 of the needle 22. Preferably, the annular interface 36 between the outer-surface 40 of the needle 22 and the inner surface 38 of the dilator 30 is minimized to inhibit the flow of blood or its constituents (or other bodily fluids) into the annular interface 36 between the dilator 30 and needle 22. Advantageously, this feature minimizes the blood's exposure to multiple external surfaces and reduces the risk of contamination, infection, and clotting.

The sheath 54 is made partially or completely from clear, semi-opaque, translucent, or transparent material so that when blood flows into the needle 22, (1) through the needle side opening 34, (2) through the dilator side opening 111, and (3) into an annular space 60 between the dilator 30 and the sheath 54, the physician or healthcare provider can see the blood. This will indicate to the physician or healthcare provider that the bevel tip 108 of the needle 22 has punctured a blood vessel.

More preferably, the dilator 30 can be coaxially mounted to the needle 22 such that at least one side opening 34 disposed on the needle 22 is rotationally aligned with at least one side opening 111 on the dilator 30. In some embodiments, the needle 22 and dilator 30 may (both) have multiple side openings 34, 111 where some or all of these side openings 34, 111 can be rotationally aligned. Preferably, the needle 22 and dilator 30 maintain rotational alignment so that blood flows substantially unobstructed through the needle side opening 34 and dilator side opening 111.

While the side openings 34, 111 in the needle 22 and the dilator 30 are aligned in the embodiment illustrated in FIG. 6, the side openings alternatively can overlap with each other or can be connected via a conduit. The conduit can be formed between the side openings 111, 34 in the dilator and the needle.

In accordance with another aspect of the present invention, there is provided an interlock or interconnection between the needle 22 and at least one of the dilator 30 or dilator hub 32. The interlock or interconnection inhibits the bevel tip 108 disposed on the distal portion 106 of the needle 22 from being advanced beyond the distal end of the dilator 30 once the dilator 30 has been advanced over the needle 22 during use. The dilator 30 thus sheaths the sharp bevel tip 108 of the needle 22 to inhibit accidental needle sticks from occurring.

Figure 7A:
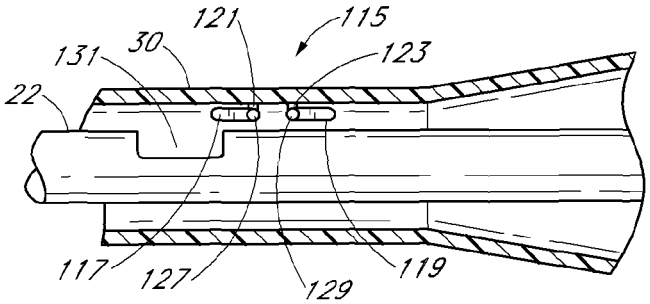
FIG. 7A is a schematic, enlarged cross-sectional view of a portion of the needle within the dilator and illustrates an embodiment of a locking mechanism configured in accordance with one aspect of the present invention.

FIG. 7A is a schematic, enlarged cross-sectional view of a portion of the needle 22 within the dilator 30 and illustrates an embodiment of a locking mechanism 115 configured in accordance with one aspect of the present invention. When engaged, the locking mechanism 115 inhibits movement of the needle 22 with respect to the dilator 30 in at least one direction. For example, the locking mechanism 115 can inhibit movement of the needle 22 at least in the distal direction once the distal tip of the needle body is drawn into the dilator portion to sheath the distal tip. The embodiment of the locking mechanism 115 illustrated in FIG. 7A comprises one or more arms or tangs 117, 119, one or more bases 121, 123, and one or more pivot couplings or hinges 127, 129.

The arm 117 may be axially aligned with the arm 119. Alternatively, the arms 117, 119 may be offset from each other in a radial direction. The arms 117, 119 may be slightly rotated relative to each other or disposed at different radial locations on the inside surface of the dilator 30. The tang or arm 117, 119 may move in a direction generally transverse to a longitudinal axis of the needle body when engaging the receptacle or hole 131.

The locking mechanism 115 is illustrated on the dilator 30. However, the needle 22 may instead comprise the locking mechanism 115. In the illustrated embodiment, the needle 22 comprises a receptacle, recess, opening, or hole 131 which interacts with the locking mechanism 115 of the dilator 30 when the needle 22 is sufficiently retracted into the dilator 30. The receptacle, recess, opening, or hole 131 may extend entirely around the needle 22 forming an annular groove or around only a portion of the needle 22.

For embodiments that have arms 117, 119 disposed at different radial locations on the inside surface of the dilator 30, the needle 22 may comprise more than one recess, opening, or hole 131. The multiple recesses, openings, or holes 131 are disposed at radial locations around the outer surface of the needle 22 that correspond to the radial spacing of the arms 117, 119 around the inside surface of the dilator 30.

The arm 117 is coupled to the base 121 via hinge 127 and rotates from an unlocked position to a locked position in a counter-clockwise direction. The arm 119 is coupled to the base 123 via hinge 129 and rotates from an unlocked position to a locked position in a clockwise direction. In the illustrated embodiment, each arm 117, 119 rotates approximately 90 degrees between the unlocked position and the locked position. However, the locked position may be more or less than 90 degrees from the unlocked position. The arms 117, 119 need only rotate a sufficient amount to allow their distal ends to abut against a portion of the perimeter of the recess, opening, or hole 131.

The recess, opening, or hole 131 in the needle 22 locally increases a gap located between an outside surface of the needle 22 and an inside surface of the dilator 30 a sufficient amount to allow the arms 117, 119 to rotate about their respective hinges 121, 123 and towards the locked position. When the arm 117 is in the locked position, the needle 22 is inhibited from relative axial movement with respect to the dilator 30 in a proximal direction. When the arm 119 is in the locked position, the needle 22 is inhibited from relative axial movement with respect to the dilator 30 in a distal direction.

The one or more bases 121, 123 are attached to or integral with the dilator 30 and extend generally towards the coaxially aligned needle 22. The bases 121, 123 are sized so as to not interfere with movement of the needle 22 through the dilator 30 while providing hinge points for attachment of the arms 117, 119. The arms 117, 119 are sized to allow movement of the needle 22 through the dilator 30 when the arms 117, 119 are in the unlocked position. The hinges 127, 129 permit the arms 117, 119 to move from the unlocked position illustrated in FIG. 7A to a locked position illustrated in FIG. 7D.

Each arm 117, 119 can separately move to the locked position when the arm 117, 119 is axially aligned with the recess, opening, or hole 131 in the needle 22. Once in the locked position, the hinge 127, 129 does not permit the arm 117, 119 to move back to the unlocked position. In some embodiments, the hinges 127, 129 slightly bias the arms 117, 119 to move towards the locked position. For example, the tang or arm 117, 119 can be biased toward the receptacle, recess, opening, or hole 131.

Figure 7B:
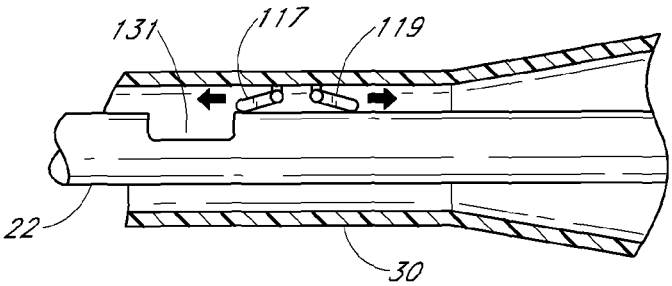
FIGS. 7B-7D illustrate the operational steps of the locking mechanism of FIG. 7A when arresting relative axial movement between the needle and the dilator.
Figure 7C:
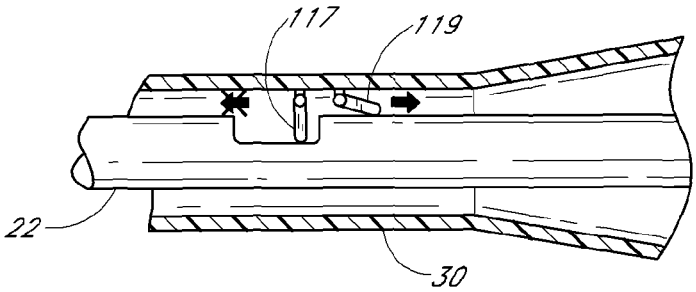
Figure 7D:
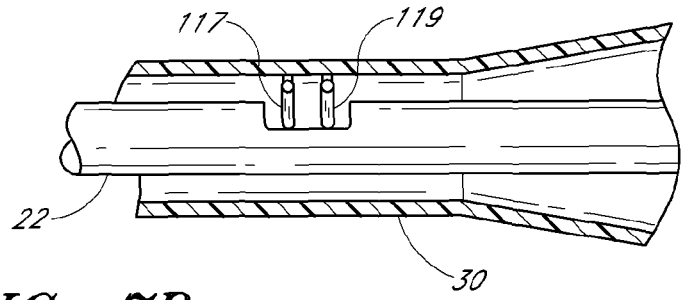

FIGS. 7B-7D illustrate the operational steps of the locking mechanism 115 of FIG. 7A when arresting relative axial movement between the needle 22 and the dilator 30. FIG. 7B illustrates the arms 117, 119 in the unlocked position. In the unlocked position, the recess, opening, or hole 131 in the needle 22 is not axial aligned with the arms 117, 119 of the locking mechanism 115. A healthcare provider can move the needle 22 with respect to the dilator 30 in both proximal and distal directions as long as the recess, opening, or hole 131 in the needle 22 stays on the proximal side of the locking mechanism 115 as is illustrated in FIG. 7B.

FIG. 7C illustrates the arm 117 in the locked position. In the locked position, the distal end of the arm 117 is disposed within the recess, opening, or hole 131 in the needle 22. Once in the locked position, the hinge 127 does not permit the arm 117 to rotate back to the unlocked position. When the arm 117 is in the locked position, the needle 22 may still move in a distal direction with respect to the dilator 32 until the recess, opening, or hole 131 is aligned with the arm 119.

FIG. 7D illustrates both arms 117, 119 in the locked position. In the dual locked position, the distal ends of the arms 117, 119 are disposed within the recess, opening, or hole 131 in the needle 22. Once in the dual locked position, the hinges 127, 129 do not permit the arms 117, 119 to rotate back to the unlocked position. When the arm 119 is in the locked position, the needle 22 is inhibited from moving in the distal direction with respect to the dilator 32.

Figure 8A:
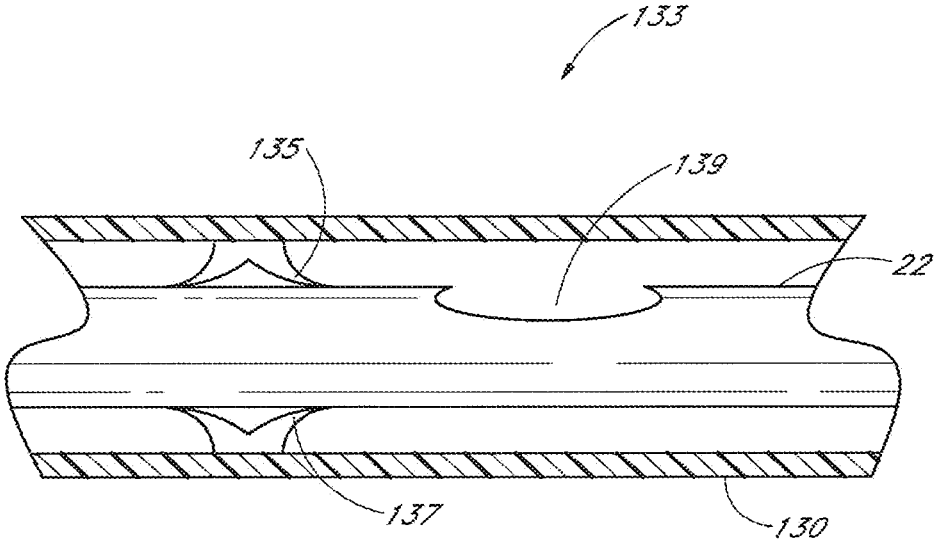
FIG. 8A is a similar cross-sectional view of a portion of a locking mechanism which is configured in accordance with another preferred embodiment of present invention.

FIG. 8A is a similar cross-sectional view of a portion of a locking mechanism 137 which is configured in accordance with another preferred embodiment of present invention. When engaged, the locking mechanism 137 inhibits movement of the needle 22 with respect to the dilator 30 in both directions. The embodiment of the locking mechanism 137 illustrated in FIG. 8A comprises one or more pairs of v-shaped arms 135, 137. The pairs of arms 135, 137 are disposed on diametrically opposite sides of the needle 22. Alternatively, the arms 135, 137 may be offset from each other in a radial direction more or less than 180 degrees apart.

The locking mechanism 133 is illustrated on the dilator 30. However, the needle 22 may instead comprise the locking mechanism 133. In the illustrated embodiment, the needle 22 comprises a recess, opening, or hole 139 which interacts with the locking mechanism 133 of the dilator 30 when the needle 22 is sufficiently retracted into the dilator 30. The receptacle, recess, opening, or hole 139 may extend entirely around the needle 22 forming an annular groove or around only a portion of the needle 22. The needle 22 may comprise more than one recess, opening, or hole 139. The multiple recesses, openings, or holes 139 are disposed at radial locations around the outer surface of the needle 22 that correspond to the radial spacing of the arms 135, 137 around the inner surface of the dilator 30.

Figure 8B:
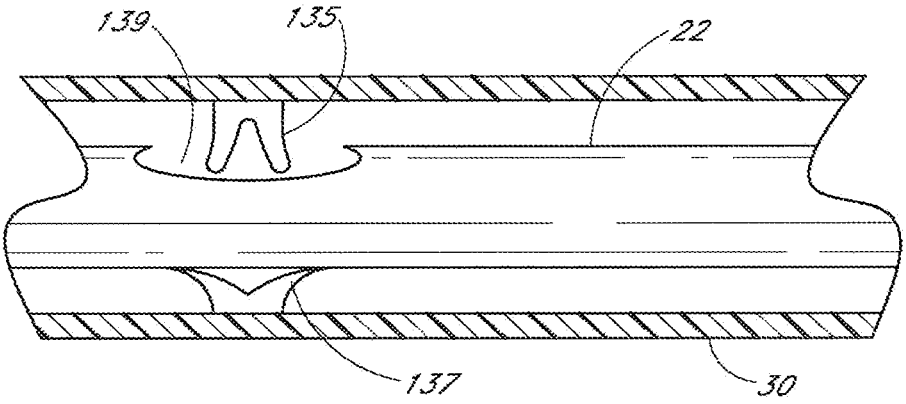
FIG. 8B illustrates the locking mechanism of FIG. 8A in a locked state.

The pairs of arms 135, 137 extend from the dilator 30 towards the needle 22. Each pair of arms 135, 137 is biased towards the needle 22 and is illustrated in a compressed or unlocked state in FIG. 8A. In the unlocked state or position, the recess, opening, or hole 139 in the needle 22 is not axial aligned with the arms 135, 137 of the locking mechanism 133. A healthcare provider can move the needle 22 with respect to the dilator 30 in both proximal and distal directions as long as the recess, opening, or hole 139 in the needle 22 stays on the proximal side of the locking mechanism 133 as is illustrated in FIG. 8B. Each pair of arms 135, 137 gently presses against the outer surface of the needle 22 as the needle 22 slides within the dilator 30 when the arms are in the unlocked state. Each pair of arms 135, 137 can rotate or bend to reach a locked state when the arms 135, 137 are axially aligned with the recess, opening, or hole 139.

In the illustrated embodiment, each arm of each pair of arms 135, 137 rotates towards the other arm between the unlocked position and the locked position. The arms 135, 137 need only be sufficiently biased so that when the arms 135, 137 align with the hole 139 their distal ends abut against a portion of the perimeter of the recess, opening, or hole 139. In the locked position, the distal ends of the arms 135, 137 are disposed within the recess, opening, or hole 139 in the needle 22.

The recess, opening, or hole 139 in the needle 22 locally increases a gap located between an outside surface of the needle 22 and an inside surface of the dilator 30 a sufficient amount to allow the arms 135, 137 to flex from their biased or unlocked state towards the locked position. FIG. 8B illustrates the pair of arms 135 of the locking mechanism 133 of FIG. 8A in a locked state. When one or both of the pair of arms 135, 137 is in the locked position the needle 22 is inhibited from relative axial movement with respect to the dilator 30 in both proximal and distal directions.

In the unlocked state Illustrated in FIG. 8A, the arms 135, 137 are biased to contact the needle 22 but not substantially interfere with movement of the needle 22 through the dilator 30. The arms 135, 137 are sized in their unbiased or locked state to inhibit movement of the needle 22 through the dilator 30. The biasing of the arms 135, 137 moves the arms 135, 137 from the unlocked position illustrated in FIG. 8A to the locked position illustrated in FIG. 8B.

Each pair of arms 135, 137 can separately move to the locked position when the pair of arms 135, 137 is axially aligned with the recess, opening, or hole 139 in the needle 22. Once in the locked position, the size and shape of the pair of arms 135, 137 inhibit movement back to the unlocked position.

Figure 9A:
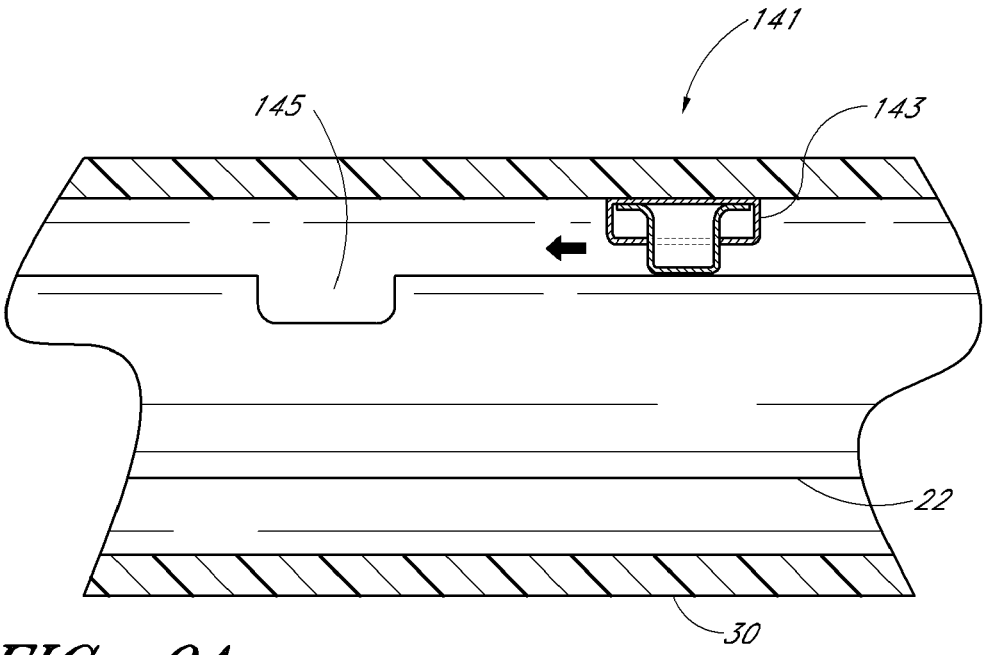
FIG. 9A is a schematic, enlarged cross-sectional view of a locking mechanism configured in accordance with an additional embodiment of the present invention.

FIG. 9A is a schematic, enlarged cross-sectional view of a locking mechanism 141 configured in accordance with an additional embodiment of the present invention. When engaged, the locking mechanism 141 inhibits movement of the needle 22 with respect to the dilator 30 in both directions. The embodiment of the locking mechanism 141 illustrated in FIG. 9A comprises a protrusion 143.

The locking mechanism 141 is illustrated on the dilator 30. However, the needle 22 may instead comprise the locking mechanism 141. In the illustrated embodiment, the needle 22 comprises a recess, opening, or hole 145 which interacts with the locking mechanism 141 of the dilator 30 when the needle 22 is sufficiently retracted into the dilator 30. The receptacle, recess, opening, or hole 145 may extend entirely around the needle 22 forming an annular groove or around only a portion of the needle 22. The needle 22 may comprise more than one recess, opening, or hole 145.

The protrusion 143 extends from the dilator 30 towards the needle 22 and is biased towards the needle 22. FIG. 9A illustrates the protrusion 143 in a compressed or unlocked state. In the unlocked state or position, the recess, opening, or hole 145 in the needle 22 is not axial aligned with the protrusion 143 of the locking mechanism 141. A healthcare provider can move the needle 22 with respect to the dilator 30 in both proximal and distal directions as long as the recess, opening, or hole 145 in the needle 22 stays on the proximal side of the locking mechanism 141 as is illustrated in FIG. 9A. The protrusion 143 gently presses against the outer surface of the needle 22 as the needle 22 slides within the dilator 30 when the locking mechanism 141 is in the unlocked state. At least a portion of the protrusion 143 can extend to reach a locked state when the protrusion 143 is axially aligned with the recess, opening, or hole 145.

The protrusion 143 need only be sufficiently biased so that when the protrusion 143 aligns with the hole 145 its distal end abuts against a portion of the perimeter of the recess, opening, or hole 145. In the locked position, the distal end of the protrusion 143 is disposed within the recess, opening, or hole 145 in the needle 22.

Figure 9B:
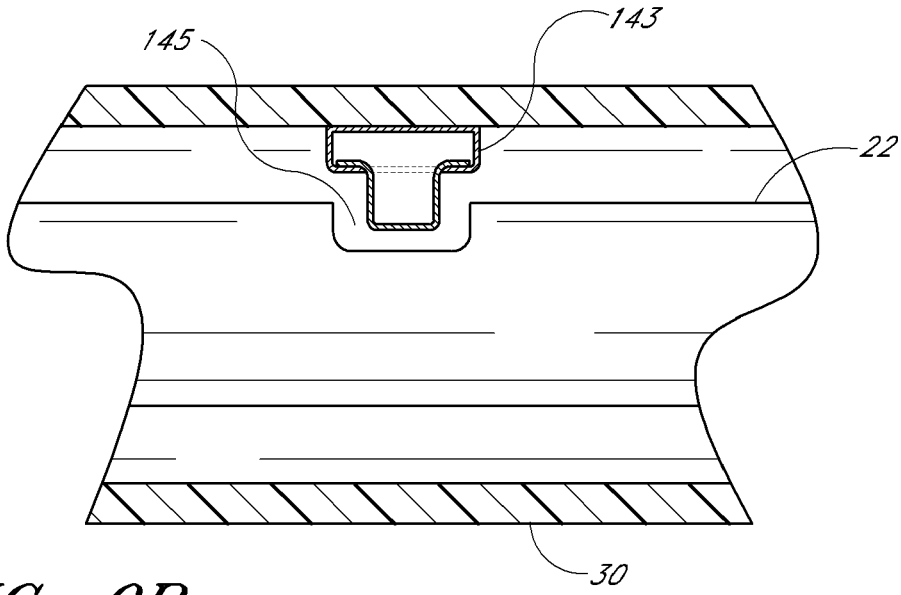
FIG. 9B illustrates the locking mechanism of FIG. 9A in a locked state.

The recess, opening, or hole 145 in the needle 22 locally increases a gap located between an outside surface of the needle 22 and an inside surface of the dilator 30 a sufficient amount to allow the protrusion 143 to flex or extend from its biased or unlocked state towards the locked position. FIG. 9B illustrates the protrusion 143 of the locking mechanism 141 of FIG. 9A in a locked state. When the protrusion 143 is in the locked position the needle 22 is inhibited from relative axial movement with respect to the dilator 30 in both proximal and distal directions.

In the unlocked state Illustrated in FIG. 9A, the protrusion 143 is biased to contact the needle 22 but not substantially interfere with movement of the needle 22 through the dilator 30. The protrusion 143 is sized in its unbiased or locked state to inhibit movement of the needle 22 through the dilator 30. The biasing of the protrusion 143 moves the distal end of the protrusion from the unlocked position illustrated in FIG. 9A to the locked position illustrated in FIG. 9B.

Figure 10A:
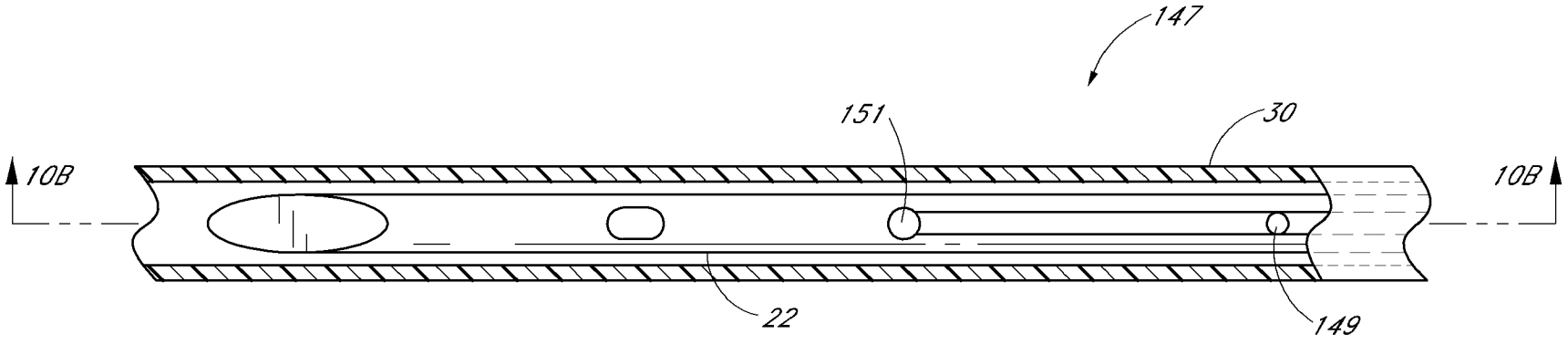
FIG. 10A is a schematic, enlarged cross-sectional view of a locking mechanism configured in accordance with a further embodiment of the present invention.

FIG. 10A is a schematic, enlarged cross-sectional view of a locking mechanism 147 configured in accordance with a further embodiment of the present invention. When engaged, the locking mechanism 141 inhibits movement of the needle 22 with respect to the dilator 30 in both directions. The embodiment of the locking mechanism 141 illustrated in FIG. 10A comprises a detent 149.

The locking mechanism 147 is illustrated on the dilator 30. However, the needle 22 may instead comprise the locking mechanism 147. In the illustrated embodiment, the needle 22 comprises a recess, opening, or hole 151 which interacts with the locking mechanism 149 of the dilator 30 when the needle 22 is sufficiently retracted into the dilator 30. The receptacle, recess, opening, or hole 151 may extend entirely around the needle 22 forming an annular groove or around only a portion of the needle 22. The needle 22 may comprise more than one recess, opening, or hole 151.

The detent 149 extends from the dilator 30 towards the needle 22 and rides in an axial groove in the needle 22. The proximal end of the groove connects with the hole 151. FIG. 10A illustrates the detent 149 in an unlocked state. In the unlocked state or position, the recess, opening, or hole 151 in the needle 22 is not axial aligned with the detent 149 of the locking mechanism 147. A healthcare provider can move the needle 22 with respect to the dilator 30 in both proximal and distal directions as long as the recess, opening, or hole 151 in the needle 22 stays on the proximal side of the locking mechanism 147 as is illustrated in FIG. 10A. The detent 149 rides in the groove in the outer surface of the needle 22 as the needle 22 slides within the dilator 30 when the locking mechanism 147 is in the unlocked state. The detent 149 and groove further inhibit relative rotation of the needle 22 with respect to the dilator 30. The detent 149 reaches a locked state when the detent 149 is axially aligned with the recess, opening, or hole 151.

Figure 10B:
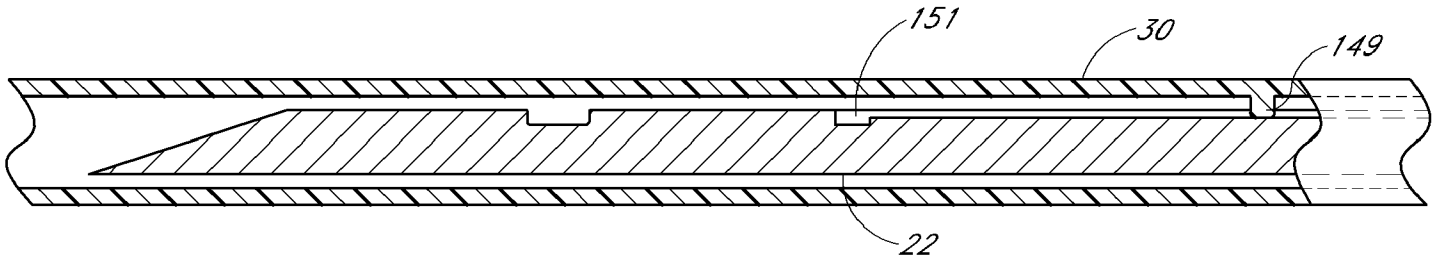
FIG. 10B is a cross-sectional view of the locking mechanism of FIG. 10A taken along lines 10B-10B.

The recess, opening, or hole 151 in the needle 22 locally increases a gap located between a bottom surface of the groove in the needle 22 and an inside surface of the dilator 30 a sufficient amount to allow the detent 149 to flex or extend from a biased or unlocked state towards the locked position. FIG. 10B illustrates the detent 149 of the locking mechanism 147 in the unlocked state. While not illustrated, when the detent 149 is in the locked position the needle 22 is inhibited from relative axial movement with respect to the dilator 30 in both proximal and distal directions.

In the unlocked state illustrated in FIGS. 10A and 10B, the detent 149 is slightly biased to contact the bottom of the groove in the needle 22 but not to substantially interfere with movement of the needle 22 through the dilator 30. The detent 149 is sized in its unbiased or locked state to inhibit movement of the needle 22 through the dilator 30.

Figure 11:
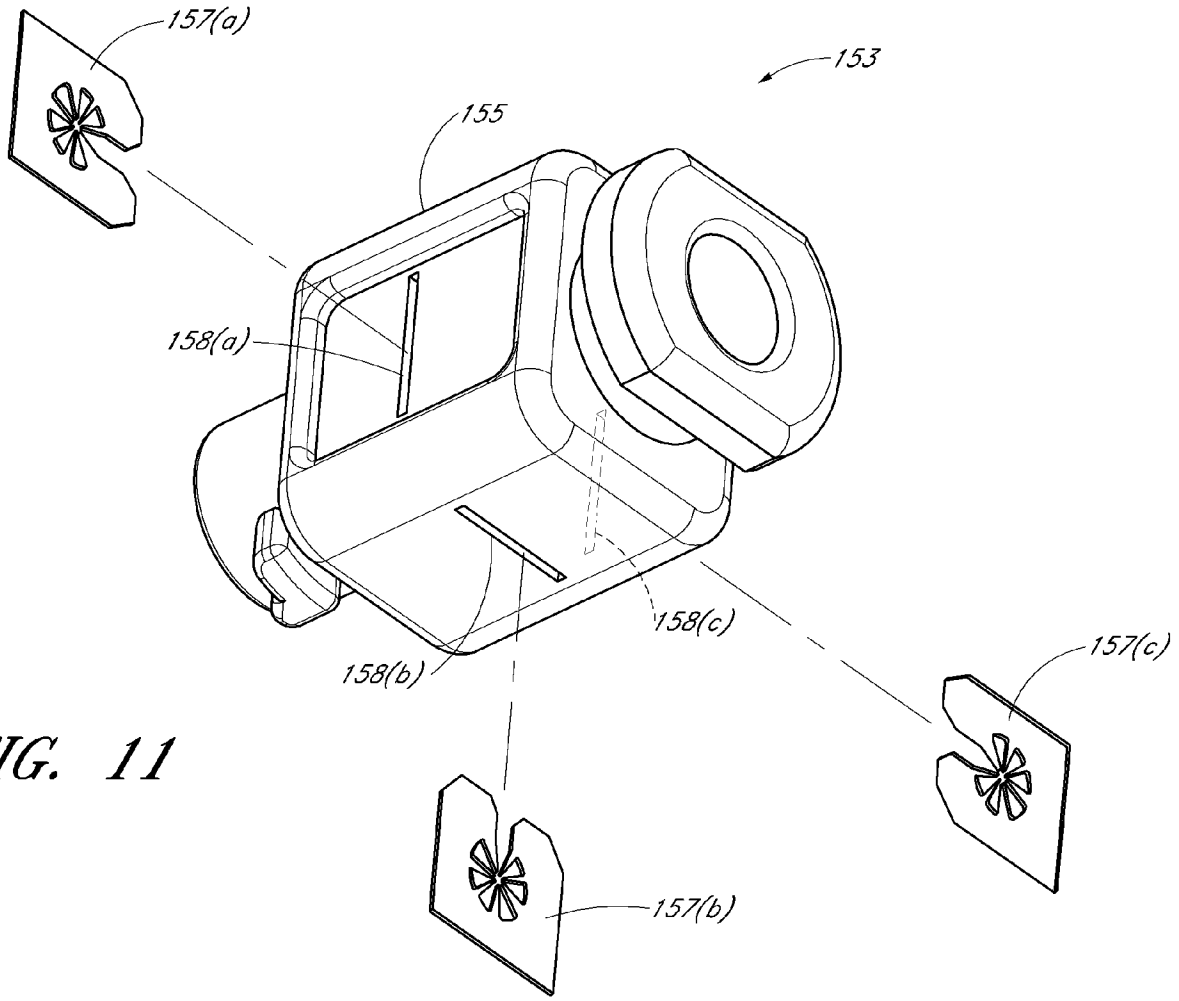
FIG. 11 is an enlarged exploded view of a dilator hub and locking plate assembly configured in accordance with an additional preferred embodiment of the present invention.

FIG. 11 is an enlarged exploded view of a dilator hub and locking plate assembly 153 configured in accordance with an additional preferred embodiment of the present invention. The assembly 153 includes a dilator hub 155 and one or more fingers or tangs 162. The one or more fingers or tangs 162 are spaced and sized such that they enter or snap into the side hole or holes in the needle 22 when the needle 22 is retracted. In some applications, a single finger or tang 162 is employed.

The one or more fingers or tangs 162 inhibit the bevel tip 108 disposed on the distal portion 106 of the needle 22 from being advanced beyond the distal end of the dilator 30 once the dilator 30 has been advanced over the needle 22 during use. The dilator 30 thus sheaths the sharp bevel tip 108 of the needle 22 to inhibit accidental needle sticks from occurring.

Figure 12A:
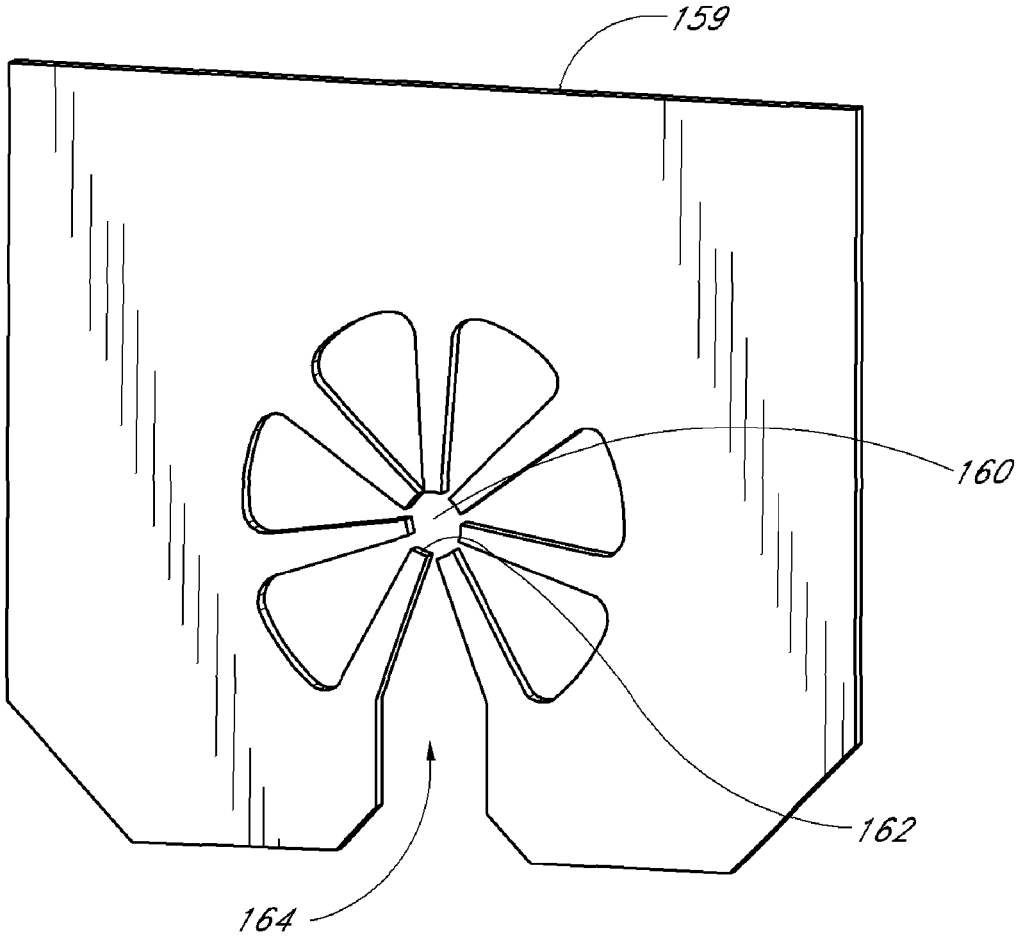
FIG. 12A is an enlarged view of an embodiment of the locking plate that can be used with the dilator hub shown in FIG. 11.
Figure 12B:
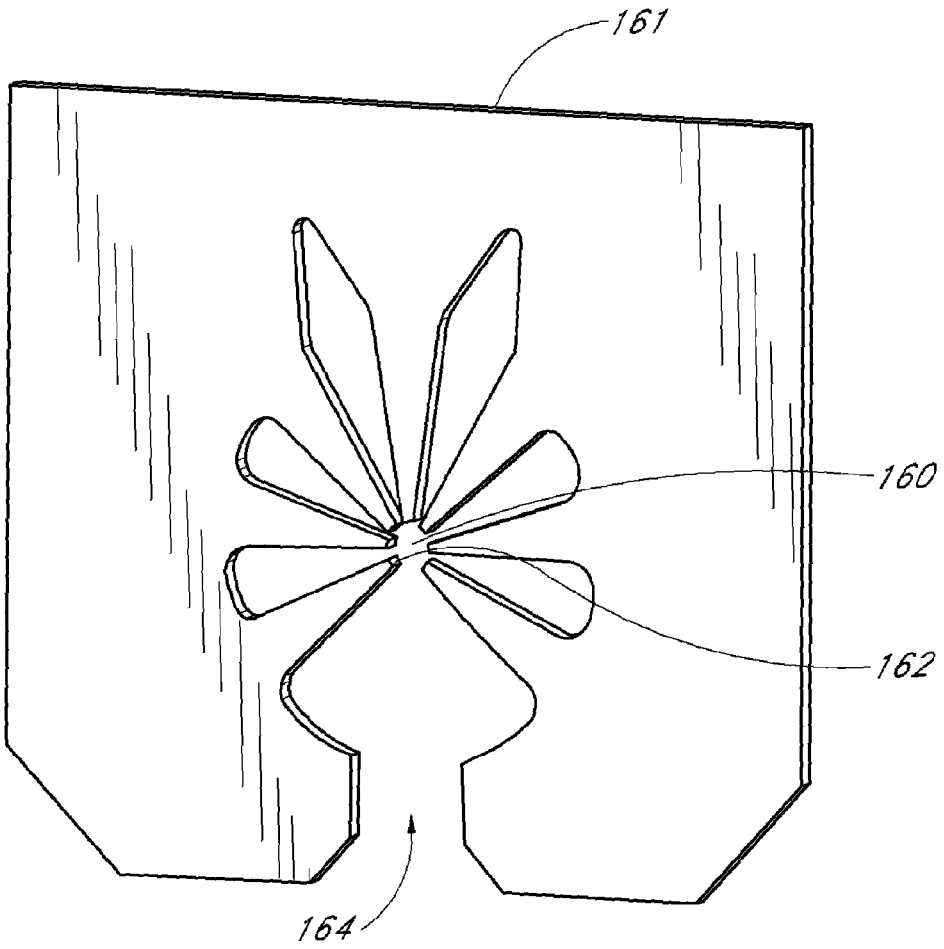
FIG. 12B is an enlarged view of another embodiment of the locking plate that can be used with the dilator hub shown in FIG. 11.
Figure 12C:
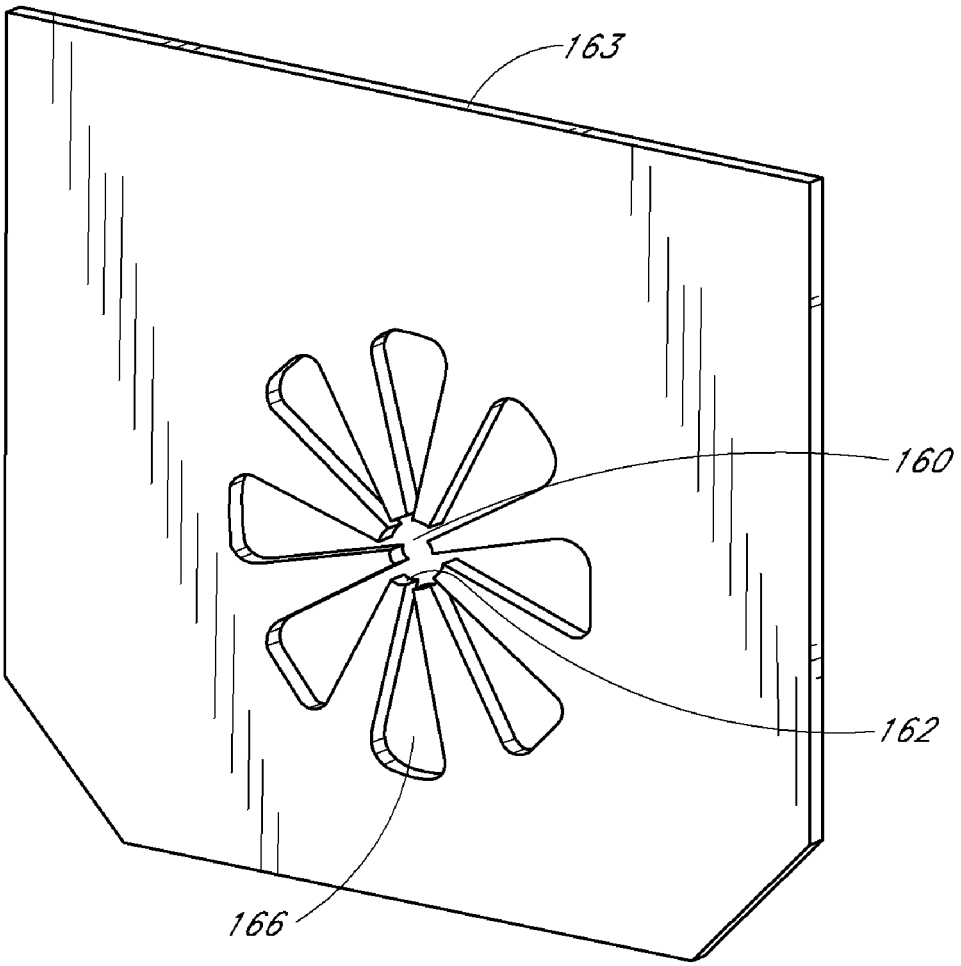
FIG. 12C is an enlarged view of an additional embodiment of the locking plate that can be used with the dilator hub shown in FIG. 11.
Figure 13A:
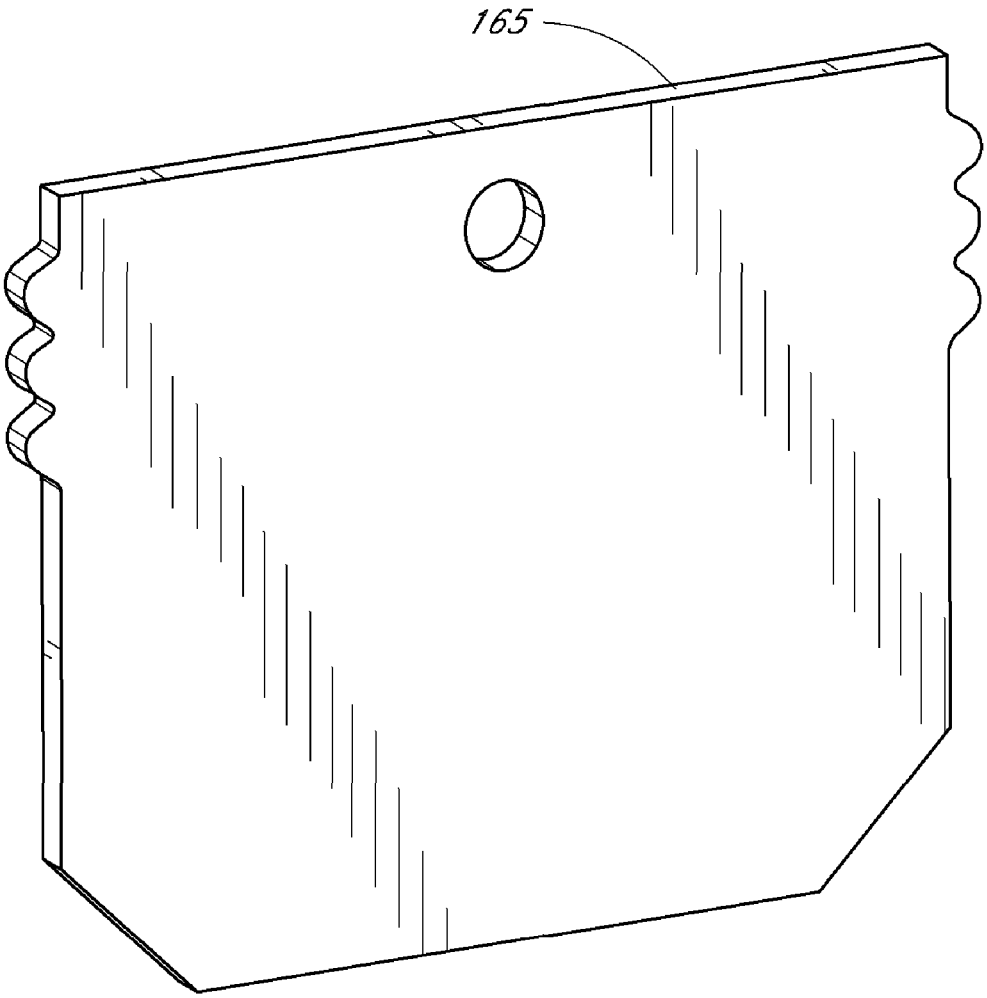
FIGS. 13A-13D are enlarged views of perimeter shapes that the locking plate can have in accordance with additional embodiments of the present invention.
Figure 13B:
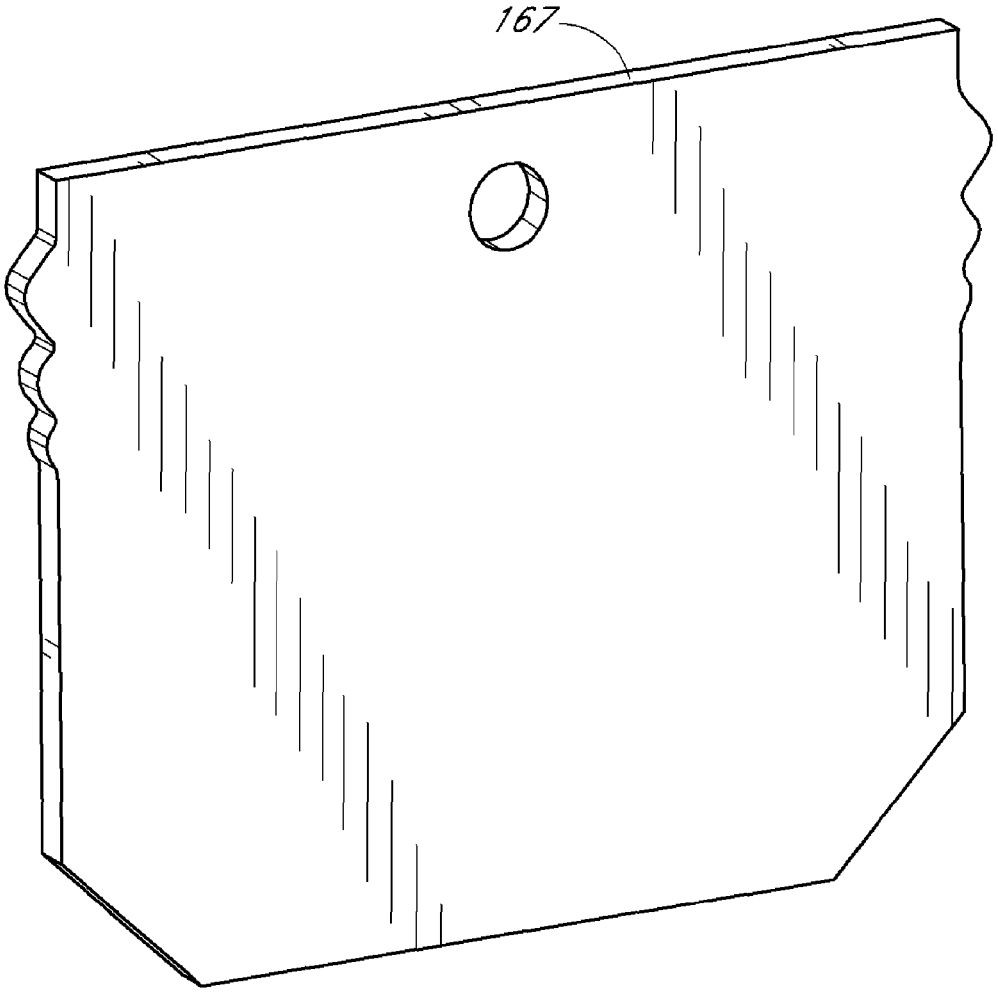
Figure 13C:
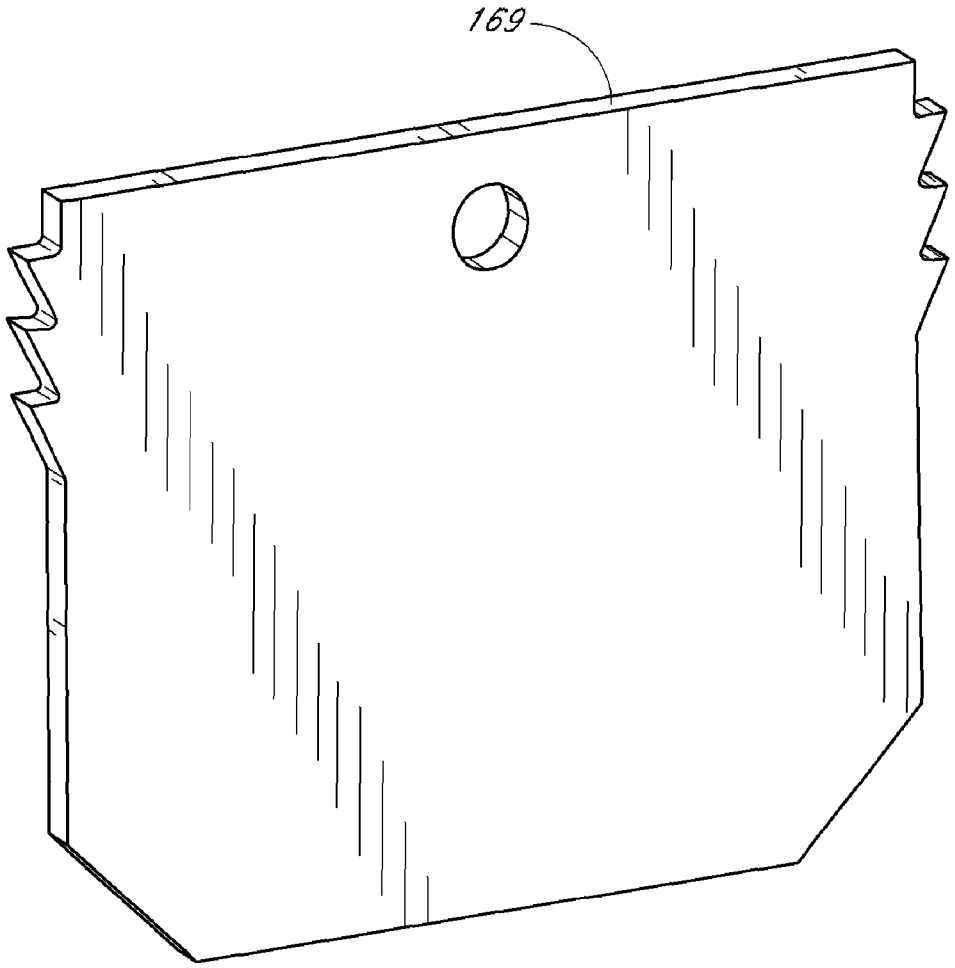
Figure 13D:
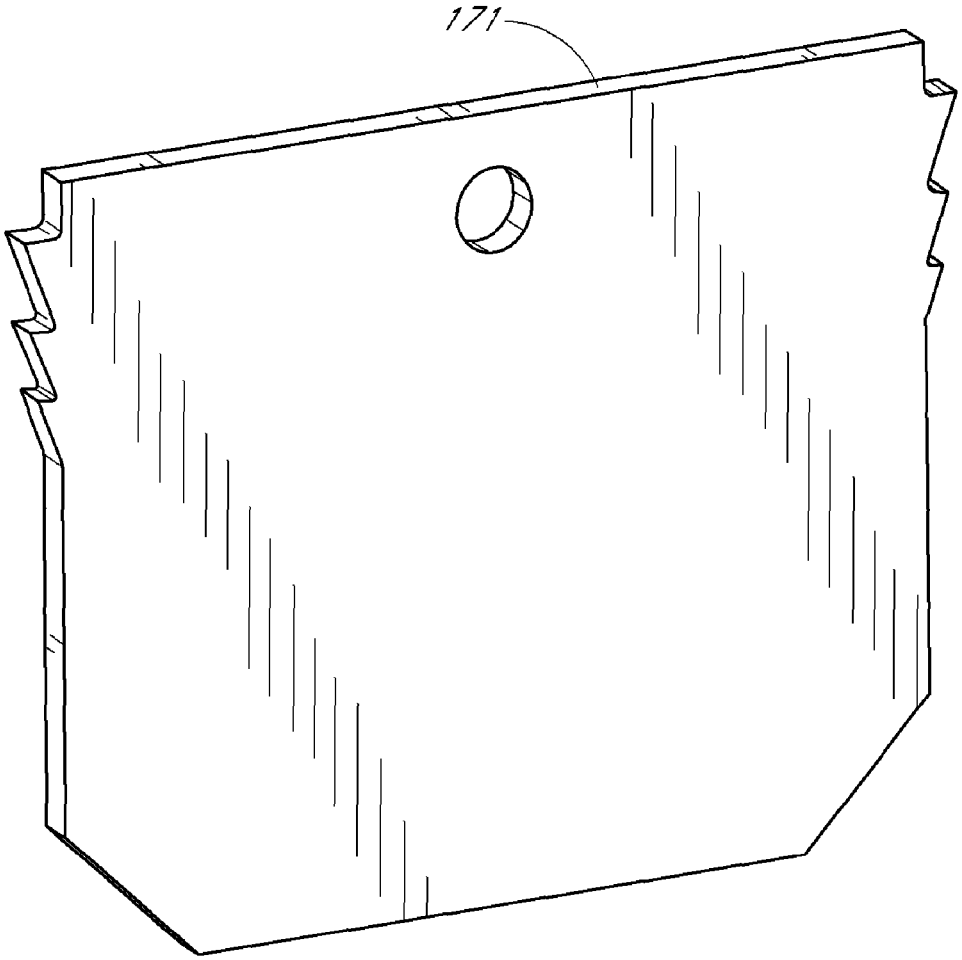

The one or more fingers or tangs 162 may be integrated into the dilator hub 155 or part of a separate structure that is combined with the dilator hub 155. In the embodiment illustrated in FIG. 11, the one or more fingers or tangs 162 are formed on a separate structure in the form of a locking plate 157(a)-(c). In this way, the locking plate 157(a)-(c) comprises the one or more fingers or tangs 162. Exemplary locking plates 157(a)-(c) are illustrated in FIGS. 12A-12C. Of course the structure of the locking plates 157(a)-(c) is not limited to the illustrated embodiments. For example, the locking plate 157 could be configured to include one or more of the locking mechanisms illustrated in FIGS. 7A, 8A, 9A, and 10A. For embodiments that have the one or more fingers or tangs 162 integrated into the dilator 155, the assembly 153 need not include a separate locking plate 157.

The dilator hub 155 and locking plate 157(a)-(c) may be separately manufactured and assembled as is illustrated in FIG. 11 or manufactured as a unitary assembly. The dilator hub 155 and locking plate 157(a)-(c) may be manufactured from the same or different materials, including, for example, plastics, metals, combinations thereof, and other materials. The locking plate 157 can be co-molded within the dilator hub 155 to form a unitary assembly. For example, a metal locking plate 157 can be molded into a plastic dilator hub 155. As explained above, a separate structure in the form of the locking plate 157 is for the In some applications, the locking plates 157(a)-(c) are movable with respect to the dilator hub 155 between unlocked and locked positions.

The dilator hub 155 is similar to the dilator hub 32 illustrated in FIG. 3A except that the dilator hub 155 is configured to slideingly receive the one or more locking plates 157(a)-(c) through one or more slots 158(a)-(c). While multiple locking plates 157(a)-(c) and slots 158(a)-(c) are illustrated in FIG. 11, only a single locking plate 157(a)-(c) and slot 158(a)-(c) can inhibit movement of the needle 22. In some applications, multiple locking plates 157(a)-(c) are inserted from different sides of the dilator hub 155 so that the fingers or tangs 162 from the locking plates 157(a)-(c) combine to completely surround the needle 22 even though separately the tangs or fingers 162 of each locking plate 157 would not surround the needle 22. The slot 158(a)-(c) need not be arranged perpendicular to the axis of the needle 22 or located in a specific side or surface of the dilator hub 155 as is illustrated in FIG. 11. Multiple locking plates 157(a)-(c) may be inserted into a single slot 158.

A healthcare provider slides the locking plate 157(a)-(c) from an unlocked position to a locked position relative to the dilator hub 155. The locking plate 157(a)-(c) may be completely removed from the slot 158(a)-(c) or partially inserted into the slot 158(a)-(c) when in the unlocked position. When the locking plate 157(a)-(c) is in the locked position, the needle 22 is disposed in a hole or center region 160 of the locking plate 157(a)-(c). The small size of the guide wire 120 inside the needle 22 does not affect the locking feature of the assembly.

FIG. 12A is an enlarged view of an embodiment of a locking plate 159 that can be used with the dilator hub 155 shown in FIG. 11. The locking plate 159 comprises a hole 160 surrounded by one or more fingers or tangs 162. An opening 164 extends from an outer perimeter of the locking plate 159 to the hole 160. The opening 164 permits the locking plate 159 to be inserted into the dilator hub 155 after the needle 22 is inserted through the dilator hub 155. The needle 22 passes through the opening 164 as the locking plate 159 is slid into the slot 158 and eventually enters the hole 160 when the locking plate 159 is in the locked position or state. Since the one or more fingers or tangs 162 do not extend entirely around the needle 22 when the needle 22 is inserted through the dilator hub 155, preferably the one or more side holes, receptacles, or annular groove in the needle 22 extend or are spaced radially about the needle 22 so that one of the fingers or tangs 162 will catch the one or more side holes, receptacles, or annular groove when the one or more side holes, receptacles, or annular groove passes through the locking plate 159.

When in the locked position, at least one of the distal ends of the fingers or tangs 162 extends a sufficient distance toward the needle 22 to enter a hole or slot in the needle 22 and inhibit further axial movement of the needle 22. In some applications, the hole or slot in the needle 22 falls onto the finger or tang 162. The hole may be the one or more side openings 34 in the side wall of the needle 22 or the receptacle, recess, opening, or hole 131, 139, 145, and 151 illustrated in, for example, FIGS. 7A, 8A, 9A, and 10A, respectively. In some applications, the receptacle, recess, opening, or hole 131, 139, 145, and 151 is the same structure as the one or more side openings 34.

FIG. 12B is an enlarged view of another embodiment of a locking plate 161 that can be used with the dilator hub 155 shown in FIG. 11. The locking plate 161 comprises a hole 160 surrounded by one or more fingers or tangs 162. An opening 164 extends from an outer perimeter of the locking plate 161 to the hole 160. The opening 164 permits the locking plate 161 to be inserted into the dilator hub 155 after the needle 22 is inserted through the dilator hub 155. The needle 22 passes through the opening 164 as the locking plate 161 is slid into the slot 158 and eventually enters the hole 160 when the locking plate 161 is in the locked position or state.

Since the one or more fingers or tangs 162 do not extend entirely around the needle 22 when the needle 22 is inserted through the dilator hub 155, preferably the one or more side holes, receptacles, or annular groove in the needle 22 extend or are spaced radially about the needle 22 so that one of the fingers or tangs 162 will catch the one or more side holes, receptacles, or annular groove when the one or more side holes, receptacles, or annular groove passes through the locking plate 161.

FIG. 12C is an enlarged view of an additional embodiment of a locking plate 163 that can be used with the dilator hub 155 shown in FIG. 11. The locking plate 163 comprises a hole 160 surrounded by one or more fingers or tangs 162. Unlike the embodiments illustrated in FIGS. 12A and 12B, the locking plate 163 has a closed pedal 166 instead of an opening. Further, the fingers or tangs 162 extend all the way around the needle 22. When the needle 22 passes through the dilator hub 155, the side hole in the needle 22 will be caught by the fingers or tangs 162 irrespective of whether the needle 22 is rotated relative to the dilator hub 155.

In this embodiment, the locking plate 163 is inserted in the dilator hub 155 before the needle 22 is axially inserted into the dilator hub 155. Since the fingers or tangs 155 extend entirely around the needle 22, a sheath or mandrel temporarily covers the side hole in the needle 22 to allow the needle 22 to be assembled through the dilator hub 155. Once assembled, the sheath or mandrel is removed from the needle 22.

FIGS. 13A-13D are enlarged views of perimeter shapes that the locking plate 157(a)-(c) can have in accordance with additional embodiments of the present invention. Any of the perimeter shapes illustrated in FIGS. 13A-D can be added to any of the locking plates 159, 161, 163. Of course the perimeter shapes are not limited to the illustrated embodiments. In some applications, the perimeter shape is selected to prevent the locking plate 157 from being removed from the dilator hub 155 or merely inhibit the locking plate 157 from falling out of the dilator hub 155.

The slot 158(a)-(c) in the dilator hub 155 would include corresponding shaped surfaces which engage with the perimeter shape 165, 167, 169, *171* of the locking plate to inhibit the healthcare provider from removing the locking plate from the dilator hub 155 once the locking plate 157 has been slid to the locked position. In this way, the healthcare provider is prevented from accidently removing the locking plate and releasing the needle 22.

The embodiments herein described are comprised of conventional, biocompatible materials. For example, the needle preferably consists of a rigid polymer or a metal such as stainless steel, nitinol, or the like. The other elements can be formed of suitable polymeric materials, such as nylon, polyethylene, high-density polyethylene, polypropylene, fluoropolymers and copolymers such as perfluoro (ethylene-propylene) copolymer, polyurethane polymers or co-polymers.

As noted above, the present access device can be used to place a catheter at other locations within a patient's body. Thus, for example, but without limitation, the access device can be used with a variety of catheters to drain fluids from abscesses, to drain air from a pneumotorax, and to access the peritoneal cavity. In such applications, body fluids flow into the viewing space to indicate when the needle has been properly placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

[1. An access device for placing a medical article within a body space, comprising:

a needle section including an elongated needle body with a sharp distal tip and a needle hub from which the needle body extends;

a medical article section comprising a tubular portion and a tube hub fixed to the tubular portion, the tubular portion being coaxially disposed and slideable over the needle body with the tube hub being disposed distal of the needle hub; and a locking mechanism disposed within the medical article section and selectively operating between the needle section and the medical article section, the locking mechanism being configured to move into a locked position from an unlocked position to arrest axial movement of the needle body at least in the distal direction once the distal tip of the needle body is drawn into the medical article section to protect the distal tip, wherein once in the locked position the locking mechanism is prevented from moving back to the unlocked position.]

[2. The access device of claim 1, wherein the locking mechanism comprises a receptacle and a tang biased toward the receptacle, the receptacle being formed on either the outer surface of the needle body or an inner surface of the tube hub, and the tang extending from the other one of the needle body outer surface and the tube hub inner surface.]

[3. The access device of claim 2, wherein the receptacle comprises a hole in the needle body.]

[4. The access device of claim 2, wherein the receptacle comprises an annular groove about the needle body.]

[5. The access device of claim 2 additionally comprising a second tang oriented to arrest axial movement of the needle body in a proximal direction.]

[6. The access device of claim 5, wherein the first and second tangs engage said receptacle when the distal tip of the needle body is sufficiently withdrawn into the medical article section.]

[7. The access device of claim 5, wherein the locking mechanism includes another receptacle disposed so as to receive the second tang when the distal tip of the needle body is withdrawn into the medical article section.]

[8. The access device of claim 2, wherein the tang is attached to the tube hub by a pivot coupling.]

[9. The access device of claim 2, wherein the tang is configured to move in a direction generally transverse to a longitudinal axis of the needle body when engaging the receptacle.]

[10. An access device for placing a medical article within a body space, comprising:

a dilator portion comprising a dilator and a dilator hub having a passageway configured to receive an elongated needle, the needle having at least one side hole;

one or more fingers or tangs disposed in the dilator hub and configured to engage with the at least one side hole at least when the needle is retracted through the passageway, wherein the one or more fingers or tangs is prevented from moving back out of engagement with the at least one side hole.]

[11. The access device of claim 10, wherein the side hole provides a passageway through which a fluid may flow.]

[12. The access device of claim 10, further comprising a dilator attached to the dilator hub, the dilator comprising a side hole that can be held in alignment with the needle side hole.]

[13. An access device for placing a medical article within a body space, comprising:

a needle section including an elongated needle body with a sharp distal tip and a needle hub from which the needle body extends;

a medical article section comprising a tubular portion and a tube hub fixed to the tubular portion, the tubular portion being coaxially disposed and slideable over the needle body with the tube hub being disposed distal of the needle hub; and a locking mechanism disposed entirely within the medical article section and selectively operating between the needle section and the medical article section, the locking mechanism being configured to arrest axial movement of the needle body at least in the distal direction once the distal tip of the needle body is drawn into the medical article to protect the distal tip.]

[14. The access device of claim 13, wherein the locking mechanism comprises a receptacle and a tang biased toward the receptacle, the receptacle being formed on either the outer surface of the needle body or an inner surface of the tube hub, and the tang extending from the other one of the needle body outer surface and the tube hub inner surface.]

[15. The access device of claim 14, wherein the receptacle comprises a hole in the needle body.]

[16. The access device of claim 14, wherein the receptacle comprises an annular groove about the needle body.]

[17. The access device of claim 14 additionally comprising a second tang oriented to arrest axial movement of the needle body in a proximal direction.]

[18. The access device of claim 17, wherein the first and second tangs engage said receptacle when the distal tip of the needle body is sufficiently withdrawn into the medical article section.]

[19. The access device of claim 17, wherein the locking mechanism includes another receptacle disposed so as to receive the second tang when the distal tip of the needle body is withdrawn into the medical article section.]

[20. The access device of claim 14, wherein the tang is attached to the tube hub by a pivot coupling.]

[21. The access device of claim 14, wherein the tang is configured to move in a direction generally transverse to a longitudinal axis of the needle body when engaging the receptacle.]

*22. An access device for placing a medical article within a body space, comprising:*

*a needle section including an elongated needle body with a sharp distal tip and a needle hub from which the needle body extends, the sharp distal tip forming an opening and the needle body comprising a side wall defining at least one side opening therein;*

*a medical article section comprising a tubular portion and a tube hub fixed to the tubular portion, the tubular portion being coaxially disposed and slideable over the needle body with the tube hub being disposed distal of the needle hub; and*

*a locking mechanism disposed within the medical article section and selectively operating between the needle section and the medical article section, the locking mechanism being configured to move into a locked position from an unlocked position to arrest axial movement of the needle body at least in the distal direction once the distal tip of the needle body is drawn into the medical article section to protect the distal tip, wherein once in the locked position the locking mechanism is prevented from moving back to the unlocked position, wherein the locking mechanism is configured to rotate into the locked position from the unlocked position once the distal tip of the needle body is drawn into the medical article section.*

*23. An access device for placing a medical article within a body space, comprising:*

*a needle section including an elongated needle body with a sharp distal tip and a needle hub from which the needle body extends, the sharp distal tip forming an opening and the needle body comprising a side wall defining at least one side opening therein;*

*a medical article section comprising a tubular portion and a tube hub fixed to the tubular portion, the tubular portion being coaxially disposed and slideable over the needle body with the tube hub being disposed distal of the needle hub; and*

*a locking mechanism disposed within the medical article section and selectively operating between the needle section and the medical article section, the locking mechanism being configured to move into a locked position from an unlocked position to arrest axial movement of the needle body at least in the distal direction once the distal tip of the needle body is drawn into the medical article section to protect the distal tip, wherein once in the locked position the locking mechanism is prevented from moving back to the unlocked position, wherein the locking mechanism is configured to move into the locked position from the unlocked position to arrest axial movement of the needle body, relative to the medical article section, in both a proximal direction and the distal direction once the distal tip of the needle body is drawn into the medical article section.*

*24. An access device for placing a medical article within a body space, comprising:*

*a needle section including an elongated needle body with a sharp distal tip and a needle hub from which the needle body extends, the sharp distal tip forming an opening and the needle body comprising a side wall defining at least one side opening therein;*

*a medical article section comprising a tubular portion and a tube hub fixed to the tubular portion, the tubular portion being coaxially disposed and slideable over the needle body with the tube hub being disposed distal of the needle hub; and*

*a locking mechanism disposed entirely within the medical article section and selectively operating between the needle section and the medical article section, the locking mechanism being configured to arrest axial movement of the needle body at least in the distal direction once the distal tip of the needle body is drawn into the medical article section to protect the distal tip, wherein the locking mechanism is configured to rotate into a locked position from an unlocked position once the distal tip of the needle body is drawn into the medical article section.*

*25. An access device for placing a medical article within a body space, comprising:*

*a needle section including an elongated needle body with a sharp distal tip and a needle hub from which the needle body extends, the sharp distal tip forming an opening and the needle body comprising a side wall defining at least one side opening therein;*

*a medical article section comprising a tubular portion and a tube hub fixed to the tubular portion, the tubular portion being coaxially disposed and slideable over the needle body with the tube hub being disposed distal of the needle hub; and*

*a locking mechanism disposed entirely within the medical article section and selectively operating between the needle section and the medical article section, the locking mechanism being configured to arrest axial movement of the needle body at least in the distal direction once the distal tip of the needle body is drawn into the medical article section to protect the distal tip, wherein the locking mechanism is configured to arrest axial movement of the needle body, relative to the medical article section, in both a proximal direction and the distal direction once the distal tip of the needle body is drawn into the medical article section.*

* * * * *